US012016389B2

United States Patent
Worm et al.

(10) Patent No.: US 12,016,389 B2
(45) Date of Patent: *Jun. 25, 2024

(54) AEROSOL DELIVERY DEVICE WITH INDEXING MOVEMENT

(71) Applicant: RAI Strategic Holdings, Inc., Winston-Salem, NC (US)

(72) Inventors: Steve Worm, Raleigh, NC (US); William Bryan Carr, Apex, NC (US); Timothy Thomas, High Point, NC (US); Kathryn Lynn Wilberding, High Point, NC (US); Paul Braxton, Summerfield, NC (US); Stephen B. Sears, Siler City, NC (US); Rajesh Sur, Winston-Salem, NC (US); Billy Conner, Clemmons, NC (US); Andries Sebastian, Clemmons, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 9 days.

This patent is subject to a terminal disclaimer.

(21) Appl. No.: 17/836,541

(22) Filed: Jun. 9, 2022

(65) Prior Publication Data

US 2022/0304386 A1 Sep. 29, 2022

Related U.S. Application Data

(63) Continuation of application No. 15/926,579, filed on Mar. 20, 2018, now Pat. No. 11,382,356.

(51) Int. Cl.
*A24F 40/46* (2020.01)
*A24F 40/30* (2020.01)
(Continued)

(52) U.S. Cl.
CPC .............. *A24F 40/46* (2020.01); *A24F 40/30* (2020.01); *A61M 11/042* (2014.02);
(Continued)

(58) Field of Classification Search
CPC ................................ A24F 40/46; A24F 40/50
See application file for complete search history.

(56) References Cited

U.S. PATENT DOCUMENTS

| 2,057,353 A | 10/1936 | Whittemore, Jr. |
| 2,104,266 A | 1/1938 | McCormick |

(Continued)

FOREIGN PATENT DOCUMENTS

| CA | 2979458 A1 | 1/2018 |
| CN | 1541577 | 11/2004 |

(Continued)

OTHER PUBLICATIONS

International Search Report from International Application No. PCT/IB2019/052189, dated Jul. 10, 2019.

*Primary Examiner* — Russell E Sparks
(74) *Attorney, Agent, or Firm* — WOMBLE BOND DICKINSON (US) LLP

(57) ABSTRACT

The present disclosure provides a control body, an aerosol delivery device, and a method of operating an aerosol delivery device. In various implementations, the aerosol delivery device comprises a control body having a housing, an electrical energy source located within the housing, a heating member operatively connected to the electrical energy source, an aerosol source member that includes an inhalable substance medium, and an indexing mechanism coupled to the heating member. The indexing mechanism is configured to move the heating member relative to the aerosol source member so as to sequentially heat one of two or more segments of the aerosol source member.

16 Claims, 14 Drawing Sheets

(51) Int. Cl.
*A24F 40/50* (2020.01)
*A61M 11/04* (2006.01)
*A61M 15/06* (2006.01)
A24F 40/20 (2020.01)
A61M 16/00 (2006.01)

(52) U.S. Cl.
CPC .............. *A61M 15/06* (2013.01); *A24F 40/20* (2020.01); *A24F 40/50* (2020.01); *A61M 2016/0024* (2013.01); *A61M 2205/8206* (2013.01)

(56) References Cited

U.S. PATENT DOCUMENTS

| | | | |
|---|---|---|---|
| 3,200,819 | A | 8/1965 | Gilbert |
| 3,205,863 | A | 9/1965 | Kent |
| 4,922,901 | A | 5/1990 | Brooks et al. |
| 5,060,671 | A | 10/1991 | Counts et al. |
| 5,093,894 | A | 3/1992 | Deevi et al. |
| 5,144,962 | A | 9/1992 | Counts et al. |
| 5,261,424 | A | 11/1993 | Sprinkel, Jr. |
| 5,269,327 | A | 12/1993 | Counts et al. |
| 5,388,574 | A | 2/1995 | Ingebrethsen et al. |
| 5,388,594 | A | 2/1995 | Counts et al. |
| 5,505,214 | A | 5/1996 | Collins et al. |
| 5,530,225 | A | 6/1996 | Hajaligol |
| 5,687,746 | A | 11/1997 | Rose et al. |
| 5,726,421 | A | 3/1998 | Fleischhauer et al. |
| 5,865,185 | A | 2/1999 | Collins et al. |
| 5,894,841 | A | 4/1999 | Voges |
| 6,053,176 | A | 4/2000 | Adams et al. |
| 6,125,853 | A | 10/2000 | Susa et al. |
| 6,155,268 | A | 12/2000 | Takeuchi |
| 7,117,867 | B2 | 10/2006 | Cox et al. |
| 7,832,410 | B2 | 11/2010 | Hon |
| 8,314,591 | B2 | 11/2012 | Terry et al. |
| 8,365,742 | B2 | 2/2013 | Hon |
| 8,499,766 | B1 | 8/2013 | Newton |
| 9,414,629 | B2 | 8/2016 | Egoyants et al. |
| 10,065,005 | B2 | 9/2018 | Wilder et al. |
| 10,099,020 | B2 | 10/2018 | Davidson et al. |
| 11,229,758 | B2 | 1/2022 | Davidson et al. |
| 11,382,356 | B2 * | 7/2022 | Worm .................. A61M 15/06 |
| 2002/0078951 | A1 | 6/2002 | Nichols et al. |
| 2005/0016550 | A1 | 1/2005 | Katase |
| 2005/0045198 | A1 | 3/2005 | Larson et al. |
| 2006/0196518 | A1 | 9/2006 | Hon |
| 2008/0092912 | A1 | 4/2008 | Robinson et al. |
| 2009/0095311 | A1 | 4/2009 | Hon |
| 2009/0126745 | A1 | 5/2009 | Hon |
| 2009/0188490 | A1 | 7/2009 | Hon |
| 2009/0272379 | A1 | 11/2009 | Thorens et al. |
| 2011/0094523 | A1 | 4/2011 | Thorens et al. |
| 2011/0126848 | A1 | 6/2011 | Zuber et al. |
| 2011/0155718 | A1 | 6/2011 | Greim et al. |
| 2011/0168194 | A1 | 7/2011 | Hon |
| 2011/0265806 | A1 | 11/2011 | Alarcon et al. |
| 2011/0290248 | A1 | 12/2011 | Schennum |
| 2012/0111347 | A1 | 5/2012 | Hon |
| 2012/0260927 | A1 | 10/2012 | Liu |
| 2012/0279512 | A1 | 11/2012 | Hon |
| 2013/0037041 | A1 | 2/2013 | Worm et al. |
| 2013/0056013 | A1 | 3/2013 | Terry et al. |
| 2013/0306084 | A1 | 11/2013 | Flick |
| 2014/0000638 | A1 | 1/2014 | Sebastian et al. |
| 2014/0060554 | A1 | 3/2014 | Collett et al. |
| 2014/0060555 | A1 | 3/2014 | Chang et al. |
| 2014/0096781 | A1 | 4/2014 | Sears et al. |
| 2014/0096782 | A1 | 4/2014 | Ampolini et al. |
| 2014/0202476 | A1 | 7/2014 | Egoyants et al. |
| 2014/0209105 | A1 | 7/2014 | Sears et al. |
| 2014/0253144 | A1 | 9/2014 | Novak et al. |
| 2014/0261408 | A1 | 9/2014 | DePiano et al. |
| 2014/0261486 | A1 | 9/2014 | Potter et al. |
| 2014/0261487 | A1 | 9/2014 | Chapman et al. |
| 2014/0261495 | A1 | 9/2014 | Novak et al. |
| 2014/0270727 | A1 | 9/2014 | Ampolini et al. |
| 2014/0270729 | A1 | 9/2014 | DePiano et al. |
| 2014/0270730 | A1 | 9/2014 | DePiano et al. |
| 2015/0013696 | A1 | 1/2015 | Plojoux et al. |
| 2015/0245659 | A1 | 9/2015 | DePiano et al. |
| 2016/0050975 | A1 | 2/2016 | Worm et al. |
| 2016/0158782 | A1 | 6/2016 | Henry, Jr. et al. |
| 2017/0013879 | A1 | 1/2017 | Frisbee et al. |
| 2018/0000157 | A1 | 1/2018 | Batista et al. |

FOREIGN PATENT DOCUMENTS

| | | |
|---|---|---|
| CN | 2719043 | 8/2005 |
| CN | 101557728 A | 10/2009 |
| CN | 201379072 | 1/2010 |
| CN | 102665459 A | 9/2012 |
| CN | 103720049 | 4/2014 |
| CN | 104770898 | 7/2015 |
| CN | 104872820 | 9/2015 |
| CN | 206403198 U | 8/2017 |
| CN | 207054784 U | 3/2018 |
| EP | 0 295 122 | 12/1988 |
| EP | 0 845 220 | 6/1998 |
| EP | 1 618 803 | 1/2006 |
| ES | 8503078 A1 | 2/1985 |
| GB | 2469850 | 11/2010 |
| JP | H03-232481 A | 10/1991 |
| JP | H03-277265 A | 12/1991 |
| JP | 2014-520542 A | 8/2014 |
| JP | 2014-533513 A | 12/2014 |
| RU | 2 614 615 C2 | 3/2017 |
| WO | WO 2003/034847 | 5/2003 |
| WO | WO 2004/080216 | 9/2004 |
| WO | WO 2005/099494 | 10/2005 |
| WO | WO 2007/131449 | 11/2007 |
| WO | 2016/079151 A1 | 5/2016 |

* cited by examiner

AEROSOL DELIVERY DEVICE WITH INDEXING MOVEMENT

CROSS-REFERENCE TO RELATED APPLICATIONS

This application is a continuation of U.S. patent application Ser. No. 15/926,579, filed on Mar. 20, 2018, and titled Aerosol Delivery Device with Indexing Movement, which is incorporated herein in its entirety by reference.

FIELD OF THE DISCLOSURE

The present disclosure relates to aerosol delivery articles and uses thereof for yielding tobacco components or other materials in an inhalable form. The articles may be made or derived from tobacco or otherwise incorporate tobacco for human consumption. More particularly, the disclosure provides articles wherein tobacco, a tobacco derived material, or other material is heated, preferably without significant combustion, to provide an inhalable substance, the substance, in the various implementations, being in a vapor or aerosol form.

BACKGROUND

Many smoking articles have been proposed through the years as improvements upon, or alternatives to, smoking products based upon combusting tobacco. Example alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon, which are incorporated herein by reference.

Representative products that resemble many of the attributes of traditional types of cigarettes, cigars or pipes have been marketed as ACCORD® by Philip Morris Incorporated; ALPHA™, JOYE 510™ and M4™ by InnoVapor LLC; CIRRUS™ and FLING™ by White Cloud Cigarettes; BLU™ by Fontem Ventures B.V.; COHITA™, COLIBRI™, ELITE CLASSIC™, MAGNUM™, PHANTOM™ and SENSE™ by EPUFFER® International Inc.; DUOPRO™, STORM™ and VAPORKING® by Electronic Cigarettes, Inc.; EGAR™ by Egar Australia; eGo-C™ and eGo-T™ by Joyetech; ELUSION™ by Elusion UK Ltd; EONSMOKE® by Eonsmoke LLC; FIN™ by FIN Branding Group, LLC; SMOKE® by Green Smoke Inc. USA; GREENARETTE™ by Greenarette LLC; HALLIGAN™ HENDU™ JET™, MAXXQ™ PINK™ and PITBULL™ by SMOKE STIK®; HEATBAR™ by Philip Morris International, Inc.; HYDRO IMPERIAL™ and LXE™ from Crown7; LOGIC™ and THE CUBAN™ by LOGIC Technology; LUCI® by Luciano Smokes Inc.; METRO® by Nicotek, LLC; NJOY® and ONEJOY™ by Sottera, Inc.; NO. 7™ by SS Choice LLC; PREMIUM ELECTRONIC CIGARETTE™ by PremiumEstore LLC; RAPP E-MYSTICK™ by Ruyan America, Inc.; RED DRAGON™ by Red Dragon Products, LLC; RUYAN® by Ruyan Group (Holdings) Ltd.; SF® by Smoker Friendly International, LLC; GREEN SMART SMOKER® by The Smart Smoking Electronic Cigarette Company Ltd.; SMOKE ASSIST® by Coastline Products LLC; SMOKING EVERYWHERE® by Smoking Everywhere, Inc.; V2CIGS™ by VMR Products LLC; VAPOR NINE™ by VaporNine LLC; VAPOR4LIFE® by Vapor 4 Life, Inc.; VEPPO™ by E-CigaretteDirect, LLC; VUSE® by R. J. Reynolds Vapor Company; Mistic Menthol product by Mistic Ecigs; and the Vype product by CN Creative Ltd; IQOS™ by Philip Morris International; and GLO™ by British American Tobacco. Yet other electrically powered aerosol delivery devices, and in particular those devices that have been characterized as so-called electronic cigarettes, have been marketed under the tradenames COOLER VISIONS™; DIRECT E-CIG™; DRAGONFLY™; EMIST™; EVERSMOKE™; GAMUCCI®; HYBRID FLAME™; KNIGHT STICKS™; ROYAL BLUES™; SMOKETIP®; and SOUTH BEACH SMOKE™;

Articles that produce the taste and sensation of smoking by electrically heating tobacco have suffered from inconsistent release of flavors or other inhalable materials. Electrically heated smoking devices have further been limited in many instances by requiring relatively large and/or complicated heat sources. Accordingly, it is desirable to provide a smoking article that can provide the sensations of cigarette, cigar, or pipe smoking, without substantial combustion, and that does so with more efficient performance characteristics.

BRIEF SUMMARY

In various implementations, the present disclosure provides an aerosol delivery device configured to yield an inhalable substance. In one implementation, the aerosol delivery device may comprise a control body having a housing, an electrical energy source located within the housing, a heating member operatively connected to the electrical energy source, an aerosol source member that includes an inhalable substance medium, and an indexing mechanism coupled to the heating member. The indexing mechanism may be configured to move the heating member relative to the aerosol source member so as to sequentially heat at least one of two or more segments of the aerosol source member. In some implementations, the heating member may located proximate an external surface of the aerosol source member. In some implementations, the heating member may be located proximate an internal surface of the aerosol source member. In some implementations, the indexing mechanism may be activated by a sensor configured to detect a draw on the aerosol source member. In some implementations, the indexing mechanism may be activated by a manual actuator. In some implementations, the manual actuator may comprise a click-return actuator. In some implementations, the manual actuator is configured to move with the heating member. In some implementations, the aerosol source member may be removably engaged with the control body and replaceable. In some implementations, the inhalable substance medium of the aerosol source member may comprise a solid or semi-solid inhalable substance medium. In some implementations, the inhalable substance medium may comprise an extruded substrate.

The present disclosure also provides a control body for use with an aerosol source member that includes an inhalable substance medium. In one implementation, the control body may comprise a housing, an electrical energy source located within the housing, a heating member operatively connected to the electrical energy source, and an indexing mechanism coupled to the heating member. The indexing mechanism may be configured to move the heating member relative to the aerosol source member so as to sequentially heat at least one of two or more segments of the aerosol source member. In some implementations, the indexing mechanism may be activated by a sensor configured to detect a draw on the aerosol source member. In some implementations, the indexing mechanism may be activated by a manual actuator. In some implementations, the manual actuator may comprise a click-return actuator. In some implementations, the manual actuator may be configured to move with the heating member.

The present disclosure also provides a method of operating an aerosol delivery device that includes a control body and an aerosol source member. In one implementation, the method may comprise energizing a heating member using an electrical energy source located in a housing of the control body, heating a first segment of the aerosol source member using the heating member, moving the heating member relative to the aerosol source member from a first position to a second position using an indexing mechanism, and heating a second segment of the aerosol source member using the heating member. In some implementations, heating the first and second segments of the aerosol source member may comprise initially heating an external surface of the first and second segments of the aerosol source member. In some implementations, heating the first and second segments of the aerosol source member may comprise initially heating an internal surface of the first and second segments of the aerosol source member. Some implementations may further comprise activating the indexing mechanism using a sensor configured to detect a draw on the aerosol source member. Some implementations may further comprise activating the indexing mechanism using a manual actuator. In some implementations, the manual actuator may comprise a click-return actuator. In some implementations, moving the heating member relative to the aerosol source member from a first position to a second position may comprise moving the manual actuator from a first position to a second position.

These and other features, aspects, and advantages of the present disclosure will be apparent from a reading of the following detailed description together with the accompanying drawings, which are briefly described below.

BRIEF DESCRIPTION OF THE DRAWINGS

In order to assist the understanding of implementations of the disclosure, reference will now be made to the appended drawings, in which like reference numerals refer to like elements and which are not necessarily drawn to scale. The drawings are by way of example only and should not be construed as limiting the disclosure.

DETAILED DESCRIPTION

Figure 1:
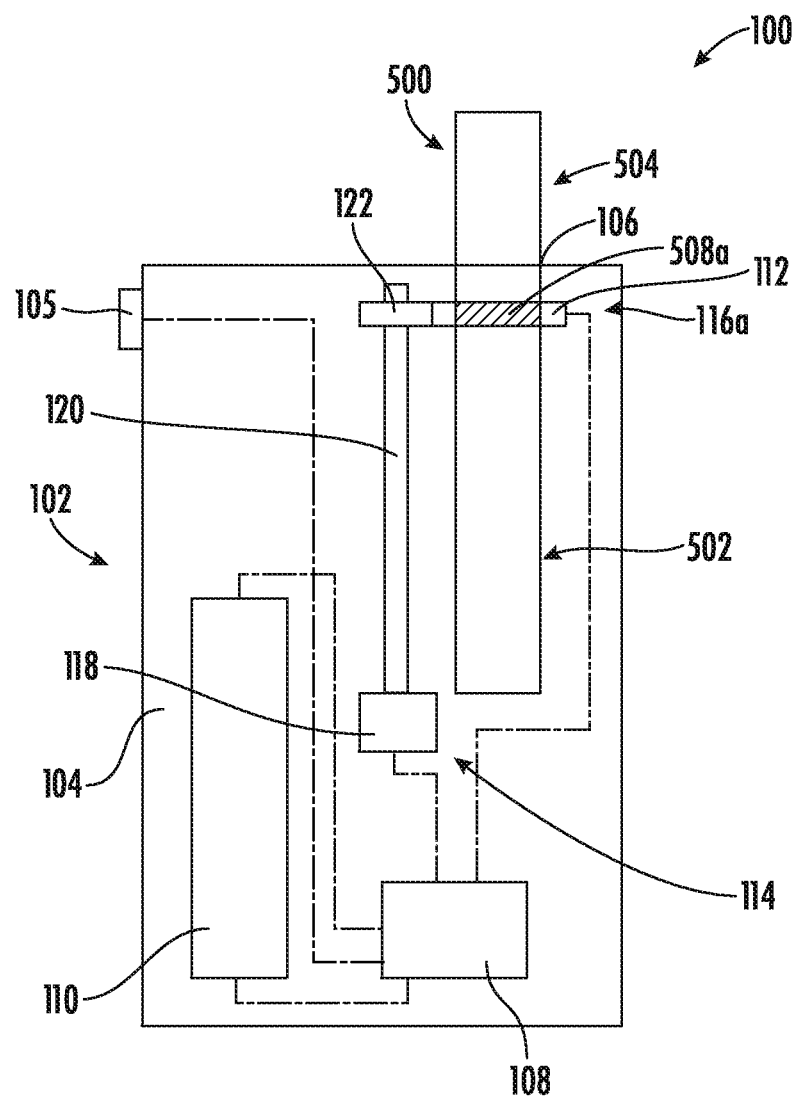
FIG. 1 schematically illustrates an aerosol delivery device including a heating member in a first heating position, in accordance with an example implementation of the present disclosure.

The present disclosure now will be described more fully hereinafter. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art. It must be noted that, as used in this specification, the singular forms "a," "an," and "the" include plural referents unless the context clearly dictates otherwise.

The present disclosure provides articles that use electrical energy to heat a material (preferably without combusting the material to any significant degree) to form an inhalable substance, the articles being sufficiently compact to be considered "hand-held" devices. In certain implementations, the articles can particularly be characterized as smoking articles. As used herein, the term is intended to mean an article that provides the taste and/or the sensation (e.g., hand-feel or mouth-feel) of smoking a cigarette, cigar, or pipe without the actual combustion of any component of the article. The term smoking article does not necessarily indicate that, in operation, the article produces smoke in the sense of the by-product of combustion or pyrolysis. Rather, smoking relates to the physical action of an individual in using the article—e.g., holding the article in a hand, drawing on one end of the article, and inhaling from the article. In further implementations, the inventive articles can be characterized as being vapor-producing articles, aerosolization articles, or pharmaceutical delivery articles. Thus, the articles can be arranged so as to provide one or more substances in an inhalable state. In other implementations, the inhalable substance can be substantially in the form of a vapor (i.e., a substance that is in the gas phase at a temperature lower than its critical point). In other implementations, the inhalable substance can be in the form of an aerosol (i.e., a suspension of fine solid particles or liquid droplets in a gas). The physical form of the inhalable substance is not necessarily limited by the nature of the inventive articles but rather may depend upon the nature of the medium and the inhalable substance itself as to whether it exists in a vapor state or an aerosol state. In some implementations, the terms may be interchangeable. Thus, for simplicity, the terms as used to describe the disclosure are understood to be interchangeable unless stated otherwise.

While the systems are generally described herein in terms of implementations associated with aerosol delivery devices such as so-called "e-cigarettes," or "tobacco heating products," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer shell or body. The overall design of the outer shell or body can vary, and the format or configuration of the outer body that can define the overall size and shape of the aerosol delivery device can vary. Typically, an elongated body resembling the shape of a cigarette or cigar can be formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. However, various other shapes and configurations may be employed in other implementations (e.g., rectangular or fob-shaped).

In one implementation, all of the components of the aerosol delivery device are contained within one outer body or shell. Alternatively, an aerosol delivery device can comprise two or more shells that are joined and are separable. For example, an aerosol delivery device can possess at one end a control body comprising a shell containing one or more reusable components (e.g., a rechargeable battery and various electronics for controlling the operation of that article), and at the other end and removably attached thereto a shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic aerosol delivery devices.

In general, aerosol delivery devices of the present disclosure may generally comprise some combination of an electrical energy source (i.e., an electrical power source), a heating member or heat generation component (e.g., a conductive electrical resistance heating member or an inductive heating member), an aerosol source member that includes an inhalable substance medium that is positionable in proximity to or in direct contact with the heating member, an indexing mechanism, and at least one control component (e.g., means for actuating, controlling, regulating and/or ceasing power for heat generation and indexing such as by controlling electrical current flow from the power source to components of the aerosol delivery device). When the heating member heats the inhalable substance medium, an inhalable substance is formed from, released from, or generated from the inhalable substance medium in a physical form suitable for inhalation by a consumer. It should be noted that the foregoing terms are meant to be interchangeable such that reference to release, releasing, releases, or released includes form or generate, forming or generating, forms or generates, and formed or generated. Specifically, the inhalable substance is released in the form of a vapor or aerosol or mixture thereof. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate an electrical energy source (e.g., a battery and/or other electrical power source, such as a capacitor) to provide current flow sufficient to provide various functionalities to the aerosol delivery device, such as powering of a heater, powering of control systems, powering of indexing mechanisms, powering of indicators, and the like. The power source can take on various implementations. Preferably, the power source is able to deliver sufficient power to rapidly heat the heating member to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices. Examples of commercially available products, for which the components thereof, methods of operation thereof, materials included therein, and/or other attributes thereof may be included in the devices of the present disclosure as well as manufacturers, designers, and/or assignees of components and related technologies that may be employed in the aerosol delivery device of the present disclosure are described in U.S. patent application Ser. No. 15/222,615, filed Jul. 28, 2016, to Watson et al., which is incorporated herein by reference in its entirety.

Although a device according to the present disclosure may take on a variety of implementations, as discussed in detail below, the use of the device by a consumer will be similar in scope. In particular, the device may be provided as a plurality of components that are combined by the consumer for use and then are dismantled by the consumer thereafter. Specifically, a consumer may have a reusable control body that is substantially cylindrical, substantially rectangular, or another shape having an opening located in a portion of the control body housing. In some implementations, the housing may also include one or more indicators of active use of the device. The consumer may further have one or more aerosol source members engage or are received in the opening of the control body. To use the article, the consumer may insert the aerosol source member into the opening or otherwise combine the aerosol source member with the control body so that the device is operable as discussed herein. In some implementations, the aerosol source member may be inserted as far into the control body as allowed by the overall structure of the components and/or other internal receiving features. Typically, at least a portion of the aerosol source member that is at least sufficiently sized for insertion into the mouth of the consumer for puffing thereon will remain outside of the control body. This may be referred to as the mouth end of the aerosol source member.

During use, the consumer initiates heating of a heating member that is adjacent an inhalable substance medium (or a specific portion thereof), and heating of the medium releases the inhalable substance within a space inside the housing and/or the aerosol source member so as to yield an inhalable substance. When the consumer inhales on the mouth end of the aerosol source member, air is drawn into the aerosol source member through openings in the control body and/or the aerosol source member itself. The combination of the drawn air and the released inhalable substance is inhaled by the consumer as the drawn materials exit the mouth end of the aerosol source member into the mouth of the consumer. In some implementations, to initiate heating, the consumer may manually actuate a pushbutton or similar component that causes the heating member to receive electrical energy from the battery or other power source. The electrical energy may be supplied for a pre-determined length of time or may be manually controlled. Preferably, flow of electrical energy does not substantially proceed in between puffs on the device (although energy flow may proceed to maintain a baseline temperature greater than ambient temperature—e.g., a temperature that facilitates rapid heating to the active heating temperature). In other implementations, heating may be initiated by the puffing action of the consumer through use of various sensors, as otherwise described herein. Once the puff is discontinued, heating may stop or be reduced. When the consumer has taken a sufficient number of puffs so as to have released a sufficient amount of the inhalable substance (e.g., an amount sufficient to equate to a typical smoking experience), the aerosol source member may be removed from the control body and discarded.

In general, relative motion between an aerosol source member and a heating member may be accomplished in a variety of ways. For example, in some implementations this may be accomplished by moving the heating member relative to the aerosol source member, and in other implementations this may be accomplished by moving the aerosol source member relative to the heating member, and in still other implementations this may be accomplished by moving both the aerosol source member and the heating member relative to each other. By way of example, in the implementations described below the relative motion is accomplished by moving the heating member relative to the aerosol source member. As will be discussed in detail below, in various implementations an indexing mechanism, coupled to the heating member, may be configured to create incremental relative motion between the heating member and the aerosol source member such that the heating member may heat one or more segments of the aerosol source member corresponding to one or more positions of the heating member relative to the aerosol source member. In some implementations, the indexing mechanism may operate "automatically" in that the indexing mechanism may be activated by one or more puffs taken by a consumer. In other implementations, the consumer may manually activate the indexing mechanism. In some implementations, a combination of automatic and manual activation may occur. In any event, once the heating member has heated the available segments of the aerosol source member, the aerosol source member may be removed from the control body and discarded. The foregoing description of use of the device can be applied to the various implementations described through minor modifications, which can be apparent to the person of skill in the art in light of the further disclosure provided herein. The above description of use, however, is not intended to limit the use of the inventive device but is provided to comply with all necessary requirements of disclosure of the present disclosure.

As noted above, at least a portion of the heated end of an aerosol source member may include an inhalable substance medium, which may comprise tobacco-containing beads, tobacco shreds, tobacco strips, reconstituted tobacco material, or combinations thereof, and/or a mix of finely ground tobacco, tobacco extract, spray dried tobacco extract, or other tobacco form mixed with optional inorganic materials (such as calcium carbonate), optional flavors, and aerosol forming materials to form a substantially solid or moldable (e.g., extrudable) substrate. Gels and suspensions may also be utilized. Some representative types of solid and semi-solid inhalable substance medium constructions and formulations are disclosed in U.S. Pat. No. 8,424,538 to Thomas et al.; U.S. Pat. No. 8,464,726 to Sebastian et al.; U.S. Pat. App. Pub. No. 2015/0083150 to Conner et al.; U.S. Pat. App. Pub. No. 2015/0157052 to Ademe et al.; and U.S. Pat. App. Pub. No. 2017-0000188 to Nordskog et al., filed Jun. 30, 2015, all of which are incorporated by reference herein.

In various implementations, the aerosol source member, or a portion thereof, may be wrapped in an overwrap material, which may be formed of any material useful for providing additional structure and/or support for the aerosol source member. In various implementations, the overwrap material may comprise a material that resists (or promotes) transfer of heat, which may include a paper or other fibrous material, such as a cellulose material. The overwrap material may also include at least one filler material imbedded or dispersed within the fibrous material. In various implementations, the filler material may have the form of water insoluble particles. Additionally, the filler material can incorporate inorganic components. In various implementations, the overwrap may be formed of multiple layers, such as an underlying, bulk layer, and an overlying layer, such as a typical wrapping paper in a cigarette. Such materials may include, for example, lightweight "rag fibers" such as flax, hemp, sisal, rice straw, and/or esparto. Further discussions relating to the configurations for overwrap materials that may be used with the present disclosure may be found in U.S. Pat. No. 9,078,473 to Worm et al., which is incorporated herein by reference in its entirety. In additional implementations, the overwrap material may have or more of the following qualities: it may be impermeable to the transfer of aerosol, it may have the ability to withstand the elevated temperature under consideration, it may promote the transfer of heat in the radial direction from the heater to the tobacco stick material, it may resist the transfer of heat in the axial direction along the tobacco stick away from the segment being heated, and/or it may have relatively low thermal mass so that it does not inhibit rapid temperature rises of the segment being heated. In one implementation, the overwrap material may be a stainless steel foil that, in some implementations, may be approximately 0.001" thick.

In various implementations, the mouth end of an aerosol source member may include a filter, which may be made of a cellulose acetate or polypropylene material. In various implementations, the filter may increase the structural integrity of the mouth end of the aerosol source member, and/or provide filtering capacity, if desired, and/or provide resistance to draw. For example, an article according to the disclosure can exhibit a pressure drop of about 50 to about 250 mm water pressure drop at 17.5 cc/second air flow. In further implementations, pressure drop can be about 60 mm to about 180 mm or about 70 mm to about 150 mm. Pressure drop value may be measured using a Filtrona Filter Test Station (CTS Series) available from Filtrona Instruments and Automation Ltd or a Quality Test Module (QTM) available from the Cerulean Division of Molins, PLC. The length of the filter at the mouth end of the aerosol source member can vary—e.g., about 2 mm to about 20 mm, about 5 mm to about 20 mm, or about 10 mm to about 15 mm. In some implementations, the filter may be separate from the overwrap, and the filter may be held in position by the overwrap.

Additional example types of overwrapping materials, wrapping material components, and treated wrapping materials that may be used in overwrap in the present disclosure are described in U.S. Pat. No. 5,105,838 to White et al.; U.S. Pat. No. 5,271,419 to Arzonico et al.; U.S. Pat. No. 5,220,930 to Gentry; U.S. Pat. No. 6,908,874 to Woodhead et al.; U.S. Pat. No. 6,929,013 to Ashcraft et al.; U.S. Pat. No. 7,195,019 to Hancock et al.; U.S. Pat. No. 7,276,120 to Holmes; U.S. Pat. No. 7,275,548 to Hancock et al.; PCT WO 01/08514 to Fournier et al.; and PCT WO 03/043450 to Hajaligol et al., which are incorporated herein by reference in their entireties. Representative wrapping materials are commercially available as R. J. Reynolds Tobacco Company Grades 119, 170, 419, 453, 454, 456, 465, 466, 490, 525, 535, 557, 652, 664, 672, 676 and 680 from Schweitzer-Maudit International. The porosity of the wrapping material can vary, and frequently is between about 5 CORESTA units and about 30,000 CORESTA units, often is between about 10 CORESTA units and about 90 CORESTA units, and frequently is between about 8 CORESTA units and about 80 CORESTA units.

To maximize aerosol and flavor delivery which otherwise may be diluted by radial (i.e., outside) air infiltration through the overwrap, one or more layers of non-porous cigarette paper may be used to envelop the aerosol source member (with or without the overwrap present). Examples of suitable non-porous cigarette papers are commercially available from Kimberly-Clark Corp. as KC-63-5, P878-5, P878-16-2 and 780-63-5. Preferably, the overwrap is a material that is substantially impermeable to the vapor formed during use of the inventive article. If desired, the overwrap can comprise a resilient paperboard material, foil-lined paperboard, metal, polymeric materials, or the like, and this material can be circumscribed by a cigarette paper wrap. The overwrap may comprise a tipping paper that circumscribes the component and optionally may be used to attach a filter material to the aerosol source member, as otherwise described herein. In various implementations, other components may exist between the inhalable substance medium and the mouth end of the aerosol source member, wherein the mouth end may include a filter. For example, in some implementations one or any combination of the following may be positioned between the inhalable substance medium and the mouth end: an air gap; phase change materials for cooling air; flavor releasing media; ion exchange fibers capable of selective chemical adsorption; aerogel particles as filter medium; and other suitable materials.

As noted above, in various implementations, the aerosol source member may include an inhalable substance medium. The inhalable substance medium may be any material that, when heated, releases an inhalable substance, such as a flavor-containing substance. In the implementation depicted in the figures, the inhalable substance medium is a solid or semi-solid substrate comprising the inhalable substance. The inhalable substance specifically may be a tobacco component or a tobacco-derived material (i.e., a material that is found naturally in tobacco that may be isolated directly from the tobacco or synthetically prepared). For example, the inhalable substance medium may comprise tobacco extracts or fractions thereof combined with an inert substrate. The inhalable substance medium may further comprise unburned tobacco or a composition containing unburned tobacco that, when heated to a temperature below its combustion temperature, releases an inhalable substance. Although less preferred, the inhalable substance medium may comprise tobacco condensates or fractions thereof (i.e., condensed components of the smoke produced by the combustion of tobacco, leaving flavors and, possibly, nicotine).

Tobacco materials useful in the present disclosure can vary and can include, for example, flue-cured tobacco, burley tobacco, Oriental tobacco or Maryland tobacco, dark tobacco, dark-fired tobacco and *Rustica* tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 7,011,096 to Li et al.; and U.S. Pat. No. 7,017,585 to Li et al.; U.S. Pat. No. 7,025,066 to Lawson et al.; U.S. Pat. App. Pub. No. 2004-0255965 to Perfetti et al.; PCT WO 02/37990 to Bereman; and Bombick et al., *Fund. Appl. Toxicol.*, 39, p. 11-17 (1997); which are incorporated herein by reference. Further example tobacco compositions that can be useful in a smoking device, including according to the present disclosure, are disclosed in U.S. Pat. No. 7,726,320 to Robinson et al., which is incorporated herein by reference in its entirety.

Still further, the inhalable substance medium may comprise an inert substrate having the inhalable substance, or a precursor thereof, integrated therein or otherwise deposited thereon. For example, a liquid comprising the inhalable substance may be coated on or absorbed or adsorbed into the inert substrate such that, upon application of heat, the inhalable substance is released in a form that can be withdrawn from the inventive article through application of positive or negative pressure. In some aspects, the inhalable substance medium may comprise a blend of flavorful and aromatic tobaccos in cut filler form. In another aspect, the inhalable substance medium may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entirety.

In some implementations, the inhalable substance medium may include tobacco, a tobacco component, and/or a tobacco-derived material that has been treated, manufactured, produced, and/or processed to incorporate an aerosol precursor composition (e.g., humectants such as, for example, propylene glycol, glycerin, and/or the like) and/or at least one flavoring agent, as well as a burn retardant (e.g., diammonium phosphate and/or another salt) configured to help prevent ignition, pyrolysis, combustion, and/or scorching of the aerosol delivery component by the heat source. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

In some implementations, other flame/burn retardant materials and additives may be included within the inhalable substance medium and my include organo-phosphorus compounds, borax, hydrated alumina, graphite, potassium tripolyphosphate, dipentaerythritol, pentaerythritol, and polyols. Others such as nitrogenous phosphonic acid salts, monoammonium phosphate, ammonium polyphosphate, ammonium bromide, ammonium borate, ethanolammonium borate, ammonium sulphamate, halogenated organic compounds, thiourea, and antimony oxides are may also be used. In each aspect of flame-retardant, burn-retardant, and/or scorch-retardant materials used in the inhalable substance medium and/or other components (whether alone or in combination with each other and/or other materials), the desirable properties are preferably provided without undesirable off-gassing, chemically reactive, or melting-type behavior. Additional flavorants, flavoring agents, additives, and other possible enhancing constituents are described in U.S. patent application Ser. No. 15/707,461 to Phillips et al., which is incorporated herein by reference in its entirety.

In addition to the inhalable substance (e.g., flavors, nicotine, or pharmaceuticals generally), the inhalable substance medium may comprise one or more aerosol-forming or vapor-forming materials, such as a polyhydric alcohol (e.g., glycerin, propylene glycol, or a mixture thereof) and/or water. Representative types of aerosol forming materials are set forth in U.S. Pat. No. 4,793,365 to Sensabaugh, Jr. et al.; and U.S. Pat. No. 5,101,839 to Jakob et al.; PCT WO 98/57556 to Biggs et al.; and *Chemical and Biological Studies on New Cigarette Prototypes that Heat Instead of Burn Tobacco*, R. J. Reynolds Tobacco Company Monograph (1988); which are incorporated herein by reference. A preferred aerosol forming material produces a visible aerosol upon the application of sufficient heat thereto, and a highly preferred aerosol forming material produces an aerosol that can be considered to be "smoke-like." Further tobacco materials, such as a tobacco aroma oil, a tobacco essence, a spray dried tobacco extract, a freeze dried tobacco extract, tobacco dust, or the like may be combined with the vapor-forming or aerosol-forming material. It is also understood that the inhalable substance itself may be in a form whereby, upon heating, the inhalable substance is released as a vapor, aerosol, or combination thereof. In other implementations, the inhalable substance may not necessarily release in a vapor or aerosol form, but the vapor-forming or aerosol-forming material that may be combined therewith can form a vapor or aerosol upon heating and function essentially as a carrier for the inhalable substance itself. Thus, the inhalable substance may be characterized as being coated on a substrate, as being absorbed in a substrate, as being adsorbed onto a surface of a substrate, or as being a natural component of the substrate (i.e., the material forming the substrate, such as a tobacco or a tobacco-derived material). Likewise, an aerosol-forming or vapor-forming material may be similarly characterized. In certain implementations, the inhalable substance medium may particularly comprise a substrate with the inhalable substance and a separate aerosol forming material included therewith. As such, in use, the substrate may be heated, the aerosol forming material may be volatilized into a vapor form taking with it the inhalable substance. In a specific example, the inhalable substance medium may comprise a solid substrate with a slurry of tobacco and an aerosol-forming material and/or vapor-forming material coated thereon or absorbed or adsorbed therein. The substrate component may be any material that does not combust or otherwise degrade at the temperatures described herein that the heating member achieves to facilitate release of the inhalable substance. For example, a paper material may be used, including a tobacco paper (e.g., a paper-like material comprising tobacco fibers and/or reconstituted tobacco). Thus, in various implementations, the inhalable substance medium may be characterized as comprising the inhalable substance, alternately as comprising the inhalable substance and a separate aerosol-former or vapor-former, alternately as comprising the inhalable substance and a substrate, or alternately as comprising the inhalable substance medium, the separate aerosol-former or vapor-former, and the substrate. Thus, the substrate may contain one or both of the inhalable substance and the aerosol-former or vapor-former.

If desired, the tobacco material or the inhalable substance medium may generally further include other components, such as sugars, glycerin, vanilla, cocoa, licorice, and other flavoring materials, such as menthol. Example plant-derived compositions that may be used are disclosed in U.S. Pat. App. Pub. No. 2012/0152265 to Dube et al., and U.S. Pat. No. 9,107,453 to Dube et al. The selection of such further components may vary based upon factors such as the sensory characteristics that are desired for the present article, and the present disclosure is intended to encompass any such further components that may be readily apparent to those skilled in the art of tobacco and tobacco-related or tobacco-derived products. See, Gutcho, *Tobacco Flavoring Substances and Methods*, Noyes Data Corp. (1972) and Leffingwell et al., *Tobacco Flavoring for Smoking Products* (1972).

The inhalable substance and/or the separate vapor forming material may be provided on the substrate in a variety of configurations. For example, both materials may be associated with the substrate such that the concentration of each material along the length of the substrate is substantially constant (e.g., when dividing the substrate into a plurality of lengthwise segments, the total concentration of material in each individual segment can be substantially similar, such as varying by less than 10%, less than 5%, or less than 2% by mass). In other implementations, one or both of the materials may be present in a defined pattern. For example, the pattern may be a gradient wherein the concentration continually increases or decreases along the length of the substrate. In this manner, the first puff on the article may provide an amount of the inhalable substance that is significantly greater than or less than the amount of the inhalable substance in the last puff. The gradient may also be designed to provide uniform production of inhalable substance across all puffs. Moreover, the pattern may be such that a bolus of inhalable substance is provided at some point along the length of the substrate (e.g., corresponding to the first puff, the last puff, or some intermediate puff on the article). Any variety of such patterns may be envisioned in light of the present disclosure, and such variations are likewise encompassed by the present disclosure. Such patterning likewise may apply to further components as described herein (e.g., flavorants). For example, a bolus of a flavorant may be provided on the substrate in a position to substantially correspond to the last puff or the last two or three puffs on the article. The release of such flavor may signal to the consumer that the final puff on the device is approaching or has been achieved. Various other configurations and components that may be included in the inhalable substance medium of the present disclosure are described in in U.S. Pat. No. 9,078,473 to Worm et al., which is incorporated herein by reference in its entirety.

In some aspects of the present disclosure, the inhalable substance medium may be configured as an extruded material, as described in U.S. Pat. App. Pub. No. 2012/0042885 to Stone et al., which is incorporated herein by reference in its entirety. In still other aspects, the inhalable substance medium may be configured as an extruded structure and/or substrate that includes, or is essentially comprised of tobacco, tobacco-related material, glycerin, water, and/or a binder material, although certain formulations exclude the binder material. In various implementations, the binder material may be any binder material commonly used for tobacco formulations including, for example, carboxymethyl cellulose (CMC), gum (e.g. guar gum), xanthan, pullulan, and/or an alginate. According to some aspects, the binder material included in the aerosol delivery component may be configured to substantially maintain a structural shape and/or integrity of the aerosol delivery component. Various representative binders, binder properties, usages of binders, and amounts of binders are set forth in U.S. Pat. No. 4,924,887 to Raker et al., which is incorporated herein by reference in its entirety.

In some implementations, the inhalable substance medium is further configured to substantially maintain its structure throughout the aerosol-generating process. That is, the inhalable substance medium is configured to substantially maintain its shape (i.e., the aerosol delivery component does not continually deform under an applied shear stress) throughout the aerosol-generating process. Although in some implementations the inhalable substance medium component may include liquids and/or some moisture content, in some implementations the inhalable substance medium is configured to remain substantially solid throughout the aerosol-generating process and substantially maintain its structural integrity throughout the aerosol-generating process. Example tobacco and/or tobacco related materials suitable for a substantially solid aerosol delivery component are described in U.S. Pat. App. Pub. No. 2015/0157052 to Ademe et al.; U.S. Pat. App. Pub. No. 2015/0335070 to Sears et al.; U.S. Pat. No. 6,204,287 to White; and U.S. Pat.

No. 5,060,676 to Hearn et al., which are all incorporated herein in their entirety by reference respectively.

In yet another aspect, the inhalable substance medium may include an extruded structure and/or substrate formed from marumarized and/or non-marumarized tobacco. Marumarized tobacco is known, for example, from U.S. Pat. No. 5,105,831 to Banerjee, et al., which is incorporated by reference herein in its entirety. Marumarized tobacco includes about 20 to about 50 percent (by weight) tobacco blend in powder form, with glycerol (at about 20 to about 30 percent weight), calcium carbonate (generally at about 10 to about 60 percent by weight, often at about 40 to about 60 percent by weight), along with binder agents, as described herein, and/or flavoring agents.

In various implementations, the substrate wall may be formed substantially of a material that can include the inhalable substance naturally therein (e.g., tobacco paper) or may be formed of any further material (e.g., paper) that can have the inhalable substance and/or the vapor-former or aerosol-former entrained therein. In addition to the inhalable substance and/or the vapor-forming or aerosol-forming substance, the substrate wall may comprise additional components. For example, a vapor barrier may be included on the outer surface of the inhalable substance medium wall. Preferably, the vapor barrier is positioned on the wall surface that is adjacent (or in contact with) the heating member when the inhalable substance medium is heated. In particular implementations, the vapor barrier may be formed of a material that is electrical insulating or may comprise a layer of electrically insulating material that can be in contact with the heating member. For example, a metal foil may be used as the vapor barrier, and the foil may have an insulating monolayer—e.g., a metal oxide layer—in contact with the heating member. the wall of the inhalable substance medium to prevent release of vapor or aerosol into the exterior volume of the inhalable substance medium and facilitate release of the vapor or aerosol into an annular space defined by the inner surface of the inhalable substance medium wall. Any vapor barrier material, such as a metal foil, may be used.

In further implementations, the inhalable substance medium may be formed of a material that softens or changes phase (especially from solid to molten) at about the working temperature of the article. For example, the inhalable substance medium may be a wax or a gel, and the inhalable substance may be entrained therein. In such implementations, it can be particularly useful to include the vapor barrier (or similar material) that provides support to the inhalable substance medium and substantially prevents the inhalable substance medium from contacting the heating member. Likewise, the inhalable substance medium may comprise a vapor barrier layer coated with an inhalable substance and/or an aerosol forming material. For example, one or more of such coating materials may be in a microencapsulated form that preferably releases its components at a temperature within one or more of the working ranges otherwise described herein. Microencapsulation technology that may be useful in such implementations is disclosed, for example, in U.S. Pat. No. 4,464,434 to Davis.

In some implementations (such as where a heating member is located within a hollow aerosol source member), tensioning of the inhalable substance medium may be useful to provide for specific performance of the inventive article. As otherwise described herein, it can be beneficial for the inhalable substance medium to have a relatively small thickness such that heat is efficiently transferred, particularly when substrates, such as paper, that exhibit relatively low heat transfer are used. Substrates of small thickness, however, can have relatively low strength in certain dimensions while exhibiting relatively high strength in other dimensions. For example, thin paper, in tension, exhibits high strength relative to the strength of the same paper in compression. Tensioning also can facilitate direct contact of the heating member to the surface of the inhalable substance medium to be heated (including a substrate that is used or a vapor barrier that may be present).

In other implementations (such as where the heating member is located around the outside of a hollow aerosol source member), it may be desirable to support the interior portion of the aerosol source member to prevent the aerosol source member from collapsing due to any outward pressure of the heating member exerted on the outside of the aerosol source member. In some implementations, for example, this may be accomplished by packing the inner diameter of the aerosol source member with shredded tobacco or other matter having a relatively low thermal mass and thermal conductivity. In other implementations, for example, this may be accomplished by relying upon the stiffness of an overwrap material (e.g., metal foil) to provide additional strength to the thin substrate wall. In other implementations, for example, a laminate may be added to the inside surface of the substrate wall with a permeable or perforated paper that will permit the transport of vapor but will provide additional stiffness to the tube wall.

As discussed above, the end of the aerosol source member opposite the mouth end is sized and shaped for insertion into the control body. A receiving chamber may thus be formed in the control body in which the greatest outer diameter (or other dimension depending upon the specific cross-sectional shape of the implementations) of the aerosol source member is preferably sized to be less than the inner diameter (or other dimension) of the open end of the receiving chamber in the control body. Ideally, the difference in the respective diameters is sufficiently small so that the aerosol source member fits snugly into the receiving chamber, and frictional forces prevent the aerosol source member from being moved without an applied force.

As noted, in some implementations, the aerosol source member may include an overwrap. When the overwrap is present, the overall length thereof can vary from being substantially identical to the length of the inhalable substance medium, up to about two times the length of the inhalable substance medium. Thus, the inhalable substance medium may have a length that is up to about 50%, up to about 30%, or up to about 10% less than the length of the overwrap. Preferably, the inhalable substance medium may have a length that is at least 10%, at least 15%, or at least 20% less than the length of the overwrap. More specifically, the distance the overwrap extends beyond the inhalable substance medium may be about 5%, about 10%, about 15%, about 20%, about 25%, about 30%, about 40%, about 50%, about 60%, about 70%, about 80%, about 90%, or about 100% of the length of the inhalable substance medium.

The overwrap also can function to provide particular characteristics at the mouth end of the cartridge. For example, the construction and/or shape and/or dimension of the overwrap can function to provide the sensation of a conventional cigarette in the mouth of a user. Moreover, as noted the overwrap may comprise a filter (e.g., cellulose acetate or polypropylene) positioned in proximity to the mouth end of the cartridge to increase the structural integrity thereof and/or to provide filtering capacity, if desired, and/or to provide resistance to draw.

Figure 2:
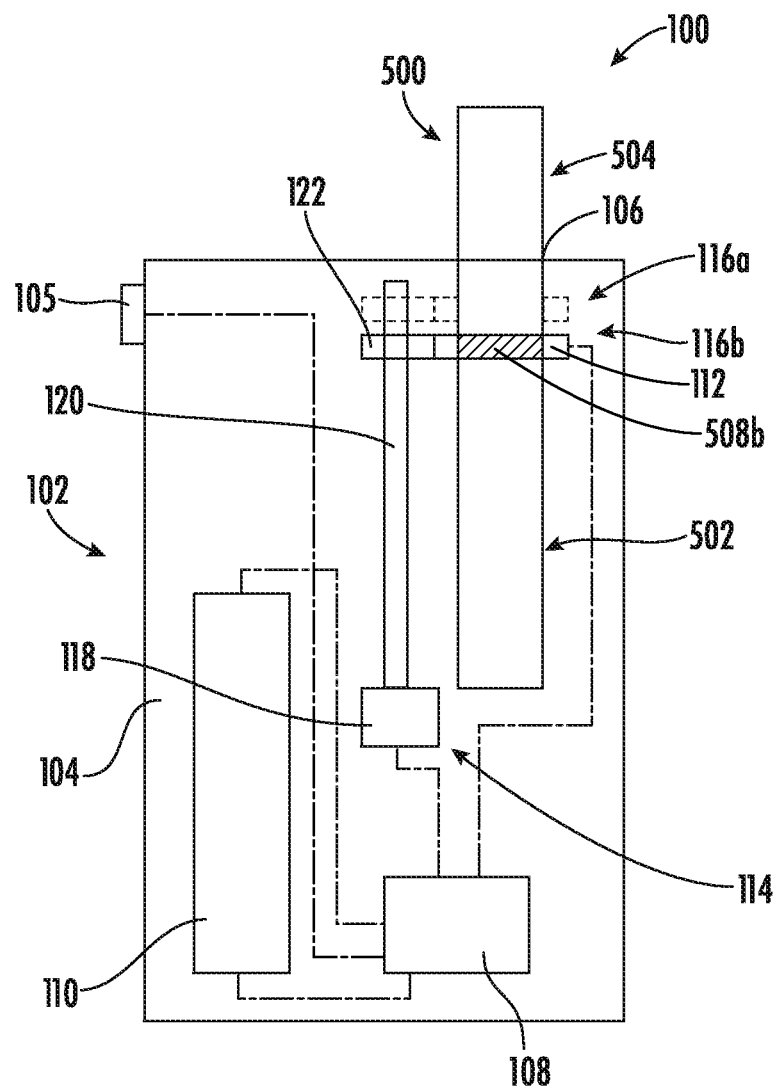
FIG. 2 schematically illustrates the aerosol delivery device of FIG. 1 showing the heating member in a second heating position, in accordance with an example implementation of the present disclosure.
Figure 3:
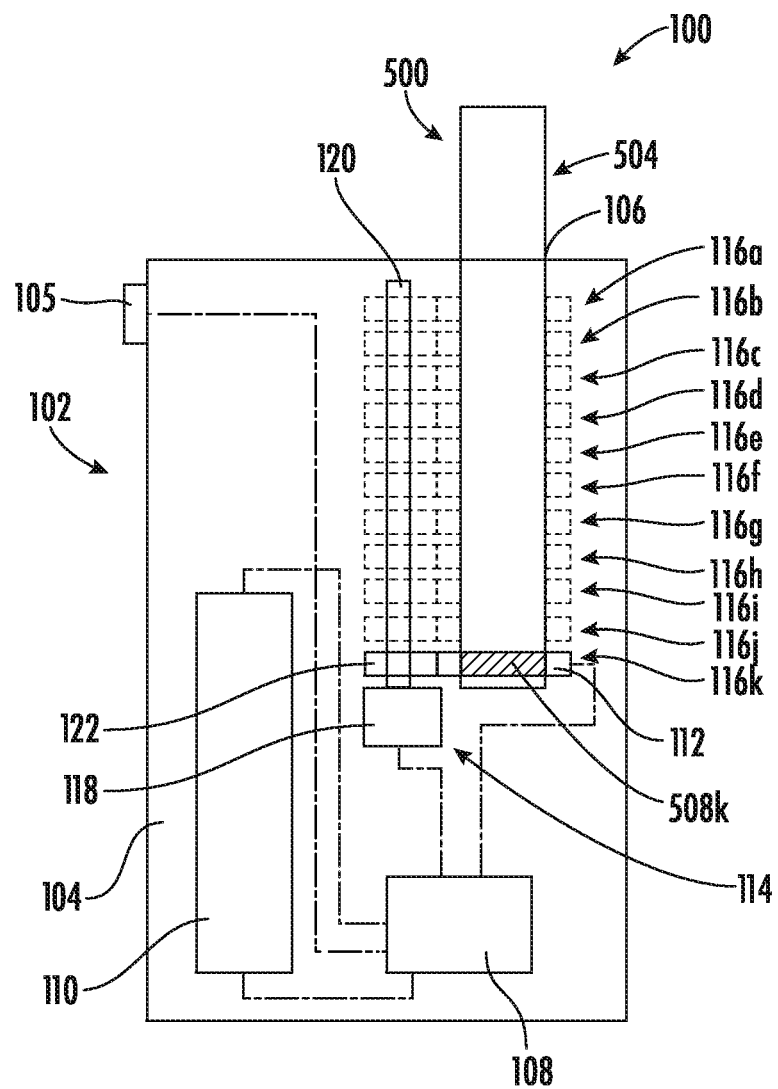
FIG. 3 schematically illustrates the aerosol delivery device of FIG. 1 showing a series of incremental heating positions, in accordance with an example implementation of the present disclosure.

A schematic illustration of an example implementation of an aerosol delivery device 100 in accordance with the present disclosure is shown in FIGS. 1-3. In general, the aerosol delivery device 100 includes a control body 102 that includes a housing 104 configured to receive an aerosol source member 500. The housing may also include a pushbutton 105 configured to activate certain operations of the device 100, such as, for example, turning on the device and initiating heating of a heating member. In various implementations, the aerosol source member 500 may comprise a heated end 502, which is configured to be inserted into the control body 102, and a mouth end 504, upon which a user draws to create the aerosol. It should be noted that while the aerosol delivery device of FIGS. 1-3 is shown as having a substantially rectangular or fob-shaped control body 102 for ease of illustration, in other implementations the control body 102 may have any other shape including an elongated shell or body that may be substantially tubular in shape and, as such, resemble the shape of a conventional cigarette or cigar, and thus the components described below may be sized and configured to fit inside an elongated body.

In various implementations, the control body 102 may be referred to as being reusable and the aerosol source member 500 may be referred to as being disposable. In some implementations, the entire device 100 may be characterized as being disposable in that the control body 102 may be configured for only a limited number of uses (e.g., until a battery power component no longer provides sufficient power to the article) with a limited number of aerosol source members 500 and, thereafter, the entire device 100, including the control body 102, may be discarded. In other implementations, the control body 102 may have a replaceable battery such that the control body 102 may be reused through a number of battery exchanges and with many aerosol source members 500. Similarly, the device 100 may be rechargeable and thus may be combined with any type of recharging technology, including connection to a typical electrical outlet, connection to a car charger (i.e., cigarette lighter receptacle), connection to a wireless charger, such as a charger that uses inductive wireless charging (including for example, wireless charging according to the Qi wireless charging standard from the Wireless Power Consortium (WPC)), or a wireless radio frequency (RF) based charger, and connection to a computer, such as through a USB cable.

In various implementations, the housing 104 may be formed of any material suitable for forming and maintaining an appropriate conformation, such as a tubular or rectangular shape, and for retaining therein an aerosol source member. In some implementations, the housing may be formed of a single wall, or multiple walls, and from a material or multiple materials (natural or synthetic) that are heat resistant so as to retain its structural integrity—e.g., does not degrade—at least at a temperature that is the heating temperature provided by the electrical heating member, as further discussed herein. In some implementations, a heat resistant polymer may be used. In other implementations, ceramic materials may be used. In further implementations, an insulating material may be used so as not to unnecessarily move heat away from the aerosol source member. The housing, when formed of a single layer, may have a thickness that preferably is about 0.2 mm to about 5.0 mm, about 0.5 mm to about 4.0 mm, about 0.5 mm to about 3.0 mm, or about 1.0 mm to about 3.0 mm. Further example types of components and materials that may be used to provide the functions described above or be used as alternatives to the materials and components noted above can be those of the types set forth in U.S. Pat. App. Pub. Nos. 2010/00186757 to Crooks et al.; 2010/00186757 to Crooks et al.; and 2011/0041861 to Sebastian et al.; the disclosures of the documents being incorporated herein by reference in their entireties.

Although not depicted in the figures, the housing 104 may include one or more apertures therein for allowing entrance of ambient air to be directed into the heated end 502 of the aerosol source member 500. Thus, when a consumer draws on the mouth end 504 of the aerosol source member 500, air can be drawn into the receiving chamber, pass into the aerosol source member 500 proximate the heated end 502, and be drawn through the inhalable substance medium for inhalation by the consumer through the mouth end 504. In implementations wherein the overwrap is present, the drawn air may carry the inhalable substance through the optional filter and out of an opening of the overwrap.

In various implementations, the control body 102 may comprise an opening 106 defined in the housing 104, a flow sensor (not shown, e.g., a puff sensor or pressure switch), a control component 108 (e.g., a microprocessor, individually or as part of a microcontroller, a printed circuit board (PCB) that includes a microprocessor and/or microcontroller, etc.), and an electrical energy source 110 (e.g., a battery, which may be rechargeable, and/or a rechargeable supercapacitor). Some examples of power sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference in their respective entireties. With respect to the flow sensor, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. Pat. No. 9,423,152 to Ampolini et al., which is incorporated herein by reference in its entirety.

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. patent application Ser. No. 14/881,392 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various implementations, and all of the foregoing disclosures are incorporated herein by reference in their entireties.

The aerosol delivery device 100 of the depicted implementation also includes a heating member 112, which receives power from the electrical energy source 110 and may be controlled by the control component 108. The heating member 112 may be any device suitable to provide heat sufficient to facilitate release of the inhalable substance for inhalation by a consumer. In certain implementations, the electrical heating member may be a resistance heating member. Useful heating members can be those having low mass, low density, and moderate resistivity and that are thermally stable at the temperatures experienced during use. Useful heating members heat and cool rapidly, and thus provide for the efficient use of energy. Rapid heating of the element also provides almost immediate volatilization of the aerosol-forming substance. Rapid cooling prevents substantial volatilization (and hence waste) of the aerosol-forming substance during periods when aerosol formation is not desired. Such heating members also permit relatively precise control of the temperature range experienced by the aerosol-forming substance, especially when time based current control is employed. Useful heating members also are chemically non-reactive (and chemically non-catalytic) with the materials comprising the inhalable substance medium being heated so as not to adversely affect the flavor or content of the aerosol or vapor that is produced. Example, non-limiting, materials that may comprise the heating member include carbon, graphite, carbon/graphite composites, metallic and non-metallic carbides, nitrides, silicides, intermetallic compounds, cermets, metal alloys, and metal foils. In particular, refractory materials may be useful. Various, different materials can be mixed to achieve the desired properties of resistivity, mass, thermal conductivity, and surface properties.

As seen in FIGS. 1-3, the electrical heating member 112 of some implementations comprises a small segment heating member that may be in direct contact with the aerosol source member 500. Direct contact may be preferred in light of the ability to provide conduction heating that is more rapid and that requires less thermal resistance. In other implementations, the heating member may have other shapes that correspond to the shape of the inhalable substance medium in the aerosol source member. Other examples of heater arrays that could be adapted for use in the present disclosure per the discussion provided above can be found in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., which are incorporated herein by reference in their entireties.

In light of the various possible heater configurations, the heating member may be constructed of an alloy of nickel, chromium, and iron, e.g., nichrome or iron, aluminum and chromium (kathal) or other alloys know to be suitable for use as a heating element. In some implementations, the heating member may be in the form of a metal foil—e.g., stainless steel foil, aluminum foil, copper foil, and the like, or may be provided in any other useful configuration, such as a significantly straight line or coiled or otherwise provided in a convoluted configuration. In a specific example, the inhalable substance medium may comprise a mix of finely ground tobacco, tobacco extract, spray dried tobacco extract, or other tobacco form mixed with optional inorganic materials (such as calcium carbonate), optional flavors, and the aerosol forming materials to form a substantially solid or moldable (e.g., extrudable) substrate, and this solid or moldable substrate then may be is direct contact with the heating member. In other implementations, however, the heating member may not be in contact with the inhalable substance medium, but, rather, may merely be proximate the inhalable substance medium.

In some implementations, heater temperature control may be provided by including a sensor such as a thermistor or thermocouple in close proximity to the heating member/substrate interface and/or by monitoring the resistance of the heating member itself and utilizing the known relationship between temperature and resistivity of the particular heating member alloy to infer the heating member temperature.

In particular implementations, a portion of the heating member may be integral with (e.g., embedded within) the inhalable substance medium. For example, the inhalable substance medium may be formed of a material as described above and may include one or more conductive materials mixed therein. Because of the presence of the conductive material in the inhalable substance medium, the application of power from the electrical energy source to the inhalable substance medium allows electrical current to flow and thus produce heat from the conductive material. Thus, the heating member may be described as being integral with the inhalable substance medium. As a non-limiting example, graphite or other suitable, conductive material may be mixed with, embedded in, or otherwise present directly on or within the material forming the inhalable substance medium to make the heating member integral with the medium. Examples of suitable heating members and related components are described in U.S. Pat. No. 9,078,473 to Worm et al., which is incorporated herein by reference.

As noted above, the control body 102 may further include a control component 108. For example, the control component may comprise a control circuit (which may be connected to further components, as further described herein) that may be connected by electrically conductive wires to the electrical energy source 110. In various implementations, the control component may control when and how the heating member 112 receives electrical energy to heat the inhalable substance medium for release of the inhalable substance for inhalation by a consumer. Such control can relate to actuation of pressure sensitive switches or the like, which are described in greater detail hereinafter. It should be noted that the terms "connected" or "coupled" should not be read as necessitating direct connection without an intervening component. Rather, these terms may encompass direct connection and/or connection via one or more intervening components. As such, in various implementations these terms may be understood to mean operatively connected to or operatively coupled with.

In various implementations, the control component 108 may also be configured to closely control the amount of heat provided to the inhalable substance medium. While the heat needed to volatilize the aerosol-forming substance in a sufficient volume to provide a desired dosing of the inhalable substance for a single puff can vary for each particular substance used, it can be particularly useful for the heating member to heat to a temperature of at least 120° C., at least 130° C., or at least 140° C. In some implementations, in order to volatilize an appropriate amount of the aerosol-forming substance and thus provide a desired dosing of the inhalable substance, the heating temperature may be at least 150° C., at least 200° C., at least 300° C., or at least 350° C. It can be particularly desirable, however, to avoid heating to temperatures substantially in excess of about 550° C. in order to avoid degradation and/or excessive, premature volatilization of the aerosol-forming substance. Heating specifically should be at a sufficiently low temperature and sufficiently short time so as to avoid significant combustion (preferably any combustion) of the inhalable substance medium. The present disclosure may particularly provide the components of the present article in combinations and modes of use that will yield the inhalable substance in desired amounts at relatively low temperatures. As such, yielding can refer to one or both of generation of the aerosol within the article and delivery out of the article to a consumer. In specific implementations, the heating temperature may be about 120° C. to about 300° C., about 130° C. to about 290° C., about 140° C. to about 280° C., about 150° C. to about 250° C., or about 160° C. to about 200° C. The duration of heating can be controlled by a number of factors, as discussed in greater detail hereinbelow. Heating temperature and duration may depend upon the desired volume of aerosol and ambient air that is desired to be drawn through the aerosol source member, as further described herein. The duration, however, may be varied depending upon the heating rate of the heating member, as the article may be configured such that the heating member is energized only until a desired temperature is reached. Alternatively, duration of heating may be coupled to the duration of a puff on the article by a consumer. Generally, the temperature and time of heating will be controlled by one or more components contained in the control body, as noted above.

It should be noted that, in some instances, the heating member and/or the segment exposed to the heating member, may transfer heat to either or both a previously heated segment or a subsequent, yet to be heated segment (i.e., "upstream and/or downstream"). As such, some implementations may include gaps or segment-insulating barriers between segments in the aerosol source member.

The amount of inhalable material released by the aerosol source member can vary based upon the nature of the inhalable material. Preferably, the aerosol source member is configured with a sufficient amount of the inhalable material, with a sufficient amount of any aerosol-former, and to function at a sufficient temperature for a sufficient time to release a desired amount over a course of use. The amount may be provided in a single inhalation from the aerosol source member or may be divided so as to be provided through a number of puffs from the article over a relatively short length of time (e.g., less than 30 minutes, less than 20 minutes, less than 15 minutes, less than 10 minutes, or less than 5 minutes). For example, the article may provide nicotine in an amount of about 0.05 mg to about 1.0 mg, about 0.08 mg to about 0.5 mg, about 0.1 mg to about 0.3 mg, or about 0.15 mg to about 0.25 mg per puff on the aerosol source member. In other implementations, a desired amount may be characterized in relation to the amount of wet total particulate matter delivered based on puff duration and volume. For example, the aerosol source member may deliver at least 1.0 mg of wet total particulate matter on each puff, for a defined number of puffs (as otherwise described herein), when smoked under standard FTC smoking conditions of 2 second, 35 ml puffs. Such testing may be carried out using any standard smoking machine. In other implementations, the amount of total particulate matter (TPM) yielded under the same conditions on each puff may be at least 1.5 mg, at least 1.7 mg, at least 2.0 mg, at least 2.5 mg, at least 3.0 mg, about 1.0 mg to about 5.0 mg, about 1.5 mg to about 4.0 mg, about 2.0 mg to about 4.0 mg, or about 2.0 mg to about 3.0 mg.

The aerosol delivery device 100 of the depicted implementation further includes an indexing mechanism 114. In various implementations, the indexing mechanism 114 may be coupled to the heating member 112 and may be configured to generate incremental relative motion between the heating member 112 and the aerosol source member 500. In the depicted implementation, the indexing mechanism 114 is coupled to the heating member 112 such that the indexing mechanism 114 moves the heating member 112 through a series of incremental heating positions so as to incrementally heat a corresponding series of segments of the aerosol source member 500. In particular, in FIG. 1, the heating member 112 is shown in a first position 116a that is configured to heat a first segment 508a of the aerosol source member 500. FIG. 2 schematically illustrates the aerosol delivery device 100 of FIG. 1 showing the heating member 112 in a second heating position 116b in accordance with an example implementation of the present disclosure. The second position 116b is configured to heat a second segment 508b of the aerosol source member. FIG. 3 schematically illustrates the aerosol delivery device 100 of FIG. 1 showing a series of incremental heating positions 116a-k in accordance with an example implementation of the present disclosure. It should be noted that while the size and spacing of the heating positions in FIGS. 1-3 are depicted as such for clarity, in various implementations the size and spacing of the heating positions may vary.

Figure 14:
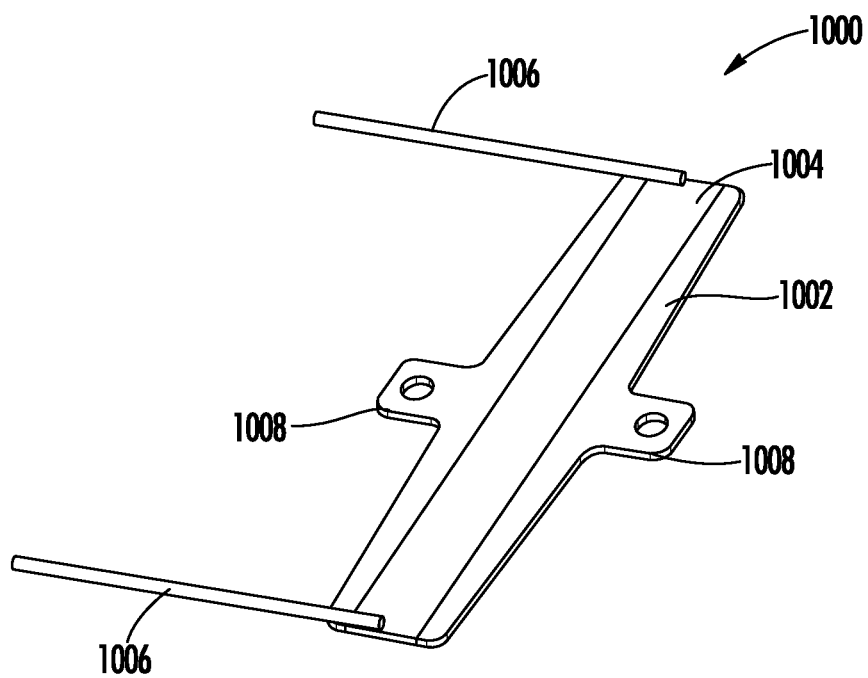
FIG. 14 illustrates a perspective view of a flexible heating member shown in a flat orientation, in accordance with an example implementation of the present disclosure.
Figure 15:
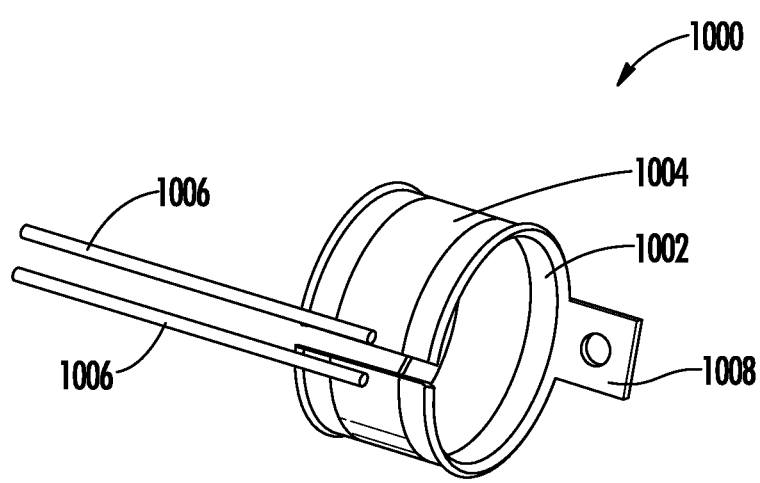
FIG. 15 illustrates a perspective view of a flexible heating member shown in a formed orientation, in accordance with an example implementation of the present disclosure.

In the depicted implementation of FIGS. 1-3, the heating member 112 comprises a structure configured to surround a portion of an outside diameter of the aerosol source member 500. In various implementations, such a structure may comprise, for example, a substantially ring-like, substantially tube-like, or substantially cylindrical structure, and may be formed of any suitable material, as described above, and preferably exhibits properties, such as described above. In one implementation, such a structure may comprise a flexible heating member configured to wrap around at least a portion of, and in some implementations, a majority of (e.g., more than 50%), and in some implementations, substantially all of, the circumference of a segment the of the aerosol source member 500. An example of a flexible heating member is depicted in FIGS. 14 and 15. In particular, FIG. 14 illustrates a perspective view of a flexible heating member 1000 shown in a flat orientation, in accordance with an example implementation of the present disclosure. In the depicted implementations, the flexible heating member 1000 includes a flexible base component 1002, a flexible heating element component 1004, a pair of heater leads 1006, and one or more mounting features 1008. In the depicted implementation, the flexible base component 1002 may comprise, for example, a polyimide film, such as for example, Kapton® developed by DuPont®.

In various implementations, the flexible heating element 1004 may comprise, for example, an etched foil heating member or a heating member printed with inks on a flexible film. In any event, the flexible base component 1002 and the flexible heating element component 1004 are configured to wrap around a portion of an aerosol source member such that activation of the flexible heating member 1000 may occur through electrical connection of the heater leads 1006 to an electrical energy source (e.g., a battery and/or other electrical power source, such as a capacitor). In various implementations, this connection may be made via a controller, such as the control component 108, to provide heating member control. As noted above, the flexible heating member 1000 of the depicted implementation also includes one or more mounting features 1008, which may be configured to allow the flexible heating member 1000 to be mounted to an indexing mechanism, such as, for example, a component of the indexing mechanism 114.

FIG. 15 illustrates a perspective view of the flexible heating member 1000 shown in a formed orientation, in accordance with an example implementation of the present disclosure. In the depicted implementation, the flexible heating member 1000 is configured to be formed in a substantially cylindrical shape (or partial cylindrical shape) such that it surrounds a portion of an outside diameter of the aerosol source member. It should be noted that in some implementations, the leads 1006 of the flexible heating member 1000 may be arranged to serve as springs, or serve a spring-like function, in order to facilitate force between the heating member 1000 and the aerosol source member 500.

Referring back to FIGS. 1-3, in the depicted implementation the indexing mechanism 114 comprises a small motor 118 (e.g., a micro stepping motor) configured to rotate a lead screw 120. Further, a carrier 122, to which the heating member 112 is affixed, is threaded through the lead screw 120. In such a manner, rotation of the lead screw 120 by the stepper motor 118 may therefor move the carrier 122, and thus the heating member 112, in a substantially linear fashion. In various implementations, the characteristics (including for example, the dimensions and/or specifications and/or control features) of the control component, stepper motor, lead screw, and carrier may be designed in order to meet a variety of performance objectives. For example, in the implementation depicted in FIGS. 1-3, the indexing mechanism 114 is configured such that the heating member 112 is moved through a series of discrete linear positions 116 relative to the aerosol source member 500. Because the aerosol source member 500 of the depicted implementation is stationary, these linear positions 116 correspond to a series of discrete segments 508 of the aerosol source member 500. As such, the control component 108, stepper motor 118, lead screw 120, carrier 122, and heating member 112 are configured such that the heating member 112 may be controlled to sequentially heat each of the segments 508 of the aerosol source member 500. With regard to the implementation of FIGS. 1-3, this represents segments 508*a-k*. It should be noted that, for purposes of clear illustration, the depicted implementation shows a total of eleven discrete positions 116*a-k* of the heating member 112, which correspond to eleven discrete segments 508*a-k* of the aerosol source member 500. In various other implementations, however, the heating member may have any number of discrete positions corresponding to any number of discrete segments of the aerosol source member, including an infinite number thereof. Further, while the implementation depicted in FIGS. 1-3 shows a plurality of discrete heating member positions 116*a-k* and corresponding discrete heated segments 508*a-k* of the aerosol source member that are spaced apart from each other, in other implementations the discrete positions and corresponding discrete segments may have different spacing, including, but not limited to, spacing that results in the discrete positions and corresponding discrete segments abutting each other and/or overlapping each other to any degree, as well as inconsistent spacing of the same.

In some implementations, movement of the heating member 112 may be initiated by the puffing action of the consumer through use of one or more various sensors, as otherwise described herein, and/or may be initiated once the puff is discontinued as sensed by one or more various sensors. Thus, in some implementations, the number of heating member positions 116 may correspond to the number of puffs available from the aerosol source member 500. In some implementations, a single aerosol source member may provide about 4 to about 12, about 5 to about 11, or about 6 to about 10 puffs, which approximates the number of puffs in a typical cigarette. In some implementations, once the heating member 112 has traveled through all of the available positions 116, the motor 118 may reverse direction and return the carrier 122 and heating member 112 to its first or starting position. In other implementations, the heating member 112 may remain at its last or final position or may be positioned at any other position or a location in between. In addition, in some implementations the controller may provide an indication (such as, for example, through a sound and/or indicator light) that the heating member 112 has traveled through all of the available positions 116. Further, in some implementations, the aerosol source member 500 may be ejected when the heating member has traveled through all of the available positions 116.

For example, in some implementations, the heating member 112 may have a close friction fit with an outer diameter of the aerosol source member 500. During normal operation, as aerosol is released from the aerosol source member 500, the heating member 112 may move from a proximal end of the aerosol source member 500 (nearest the mouth end 504) to the distal end (nearest the heated end 502). The friction between the heating element and the aerosol source member 500 may act in a direction such that friction force will be toward the control body 102 each time the heating element 112 moves from one segment to the next. In various implementations, the aerosol source member 500 may be prevented from moving in this direction by one or more stops or positioning features (not shown) located in the control unit 102. Once the heating member 112 has reached the end of its travel, the heating member 112 may be moved back to the original start position. In this case, the friction force may act in a direction outward from the control body 102. Since the aerosol source member 500 will not be prevented from traveling in this direction, it will be dragged outward by the motion of the heating member 112, and thus ejected from the control body 102.

Although across various implementations operation of an aerosol delivery device may vary, in the example implementation of FIGS. 1-3, the general operation of the aerosol delivery device 100 may occur as follows, with one or more of the following steps occurring via control from the control component 108. In a first step, the heating member 112, located at a first heating position 116 (such as for example, position 116a), may be turned on by pressing the pushbutton 105. In addition, the heating member 112 may pre-heat to a first temperature, T1, which, in some implementations, may be low enough such that aerosol is not generated from the aerosol source member 500. In a second step, the user may draw on the aerosol source member (detected, for example, by a flow sensor), and the heating member 112 may heat to a second temperature, T2, in which aerosol is generated from the aerosol source member 500. When the user stops puffing (detected, for example, by a flow sensor), the heater temperature may return to the first temperature, T1, and the indexing mechanism may automatically move to the next heating position 116 (such as, for example, position 116b). This process may continue until the heating member 112 travels to the last of the heating positions 116 (such as, for example, position 116k). After this point, the aerosol source member 500 may be ejected from the housing 102.

Figure 4:
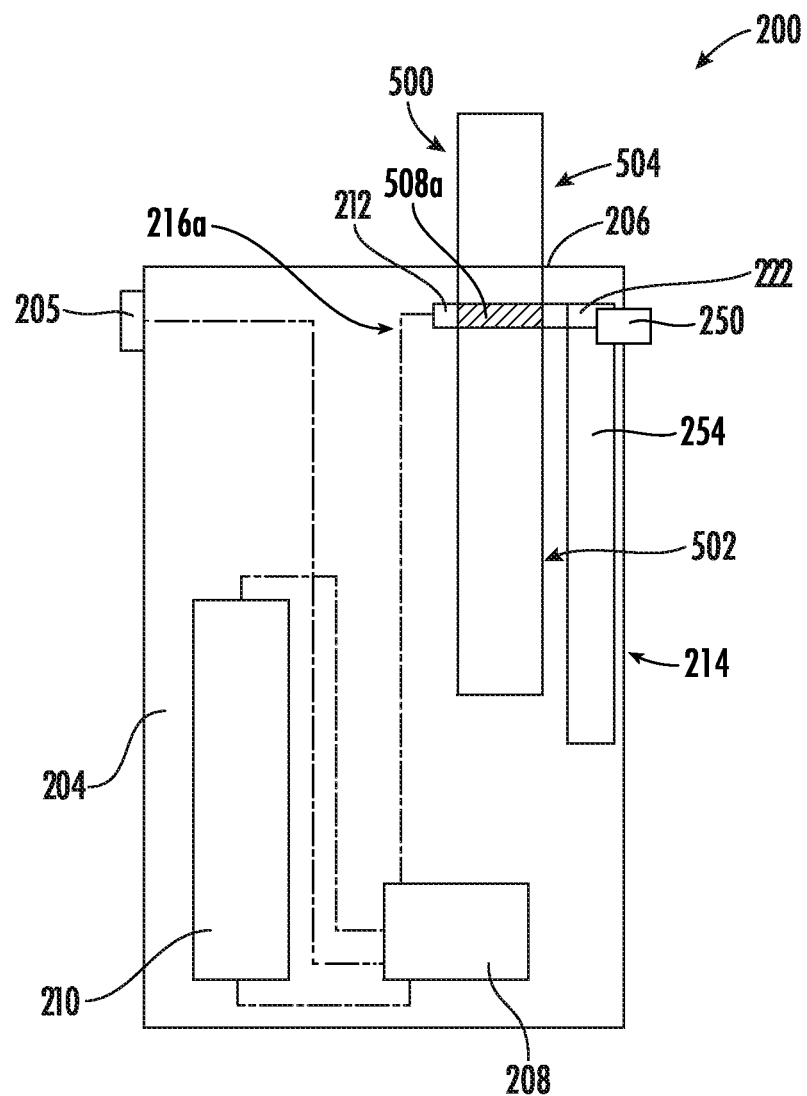
FIG. 4 schematically illustrates an aerosol delivery device including a heating member in a first heating position, in accordance with an example implementation of the present disclosure.
Figure 5:
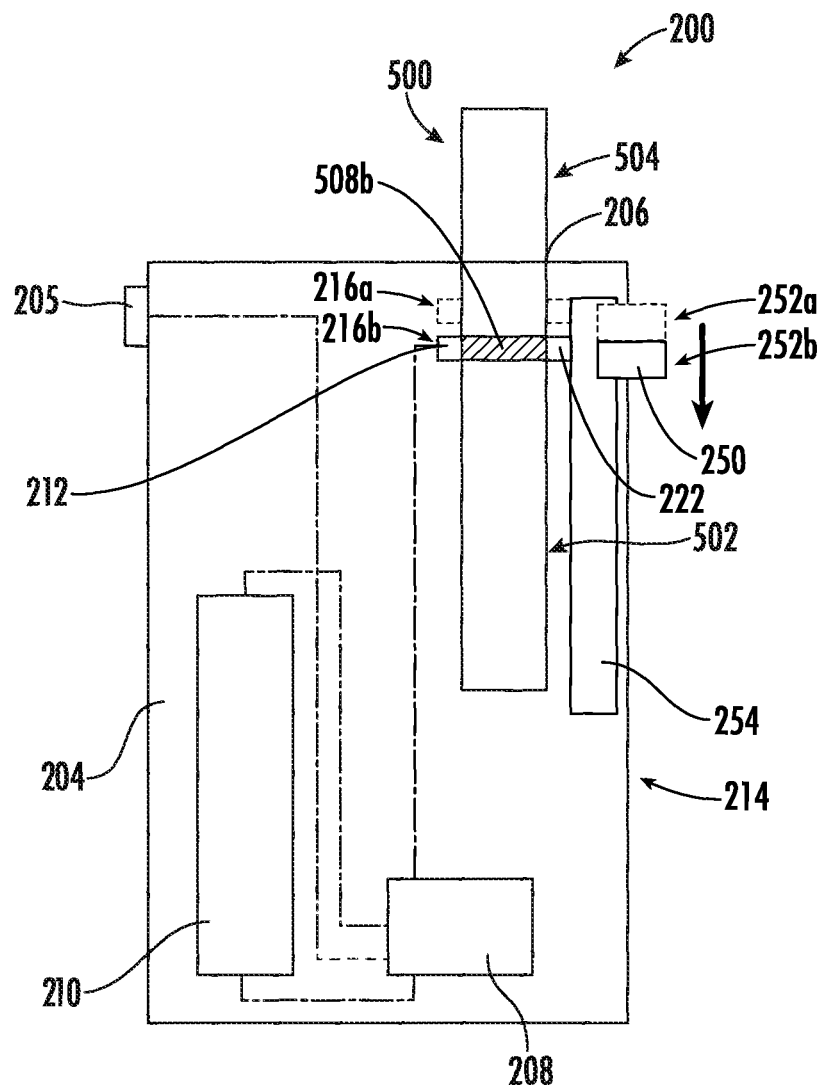
FIG. 5 schematically illustrates the aerosol delivery device of FIG. 4 showing the heating member in a second heating position, in accordance with an example implementation of the present disclosure.
Figure 6:
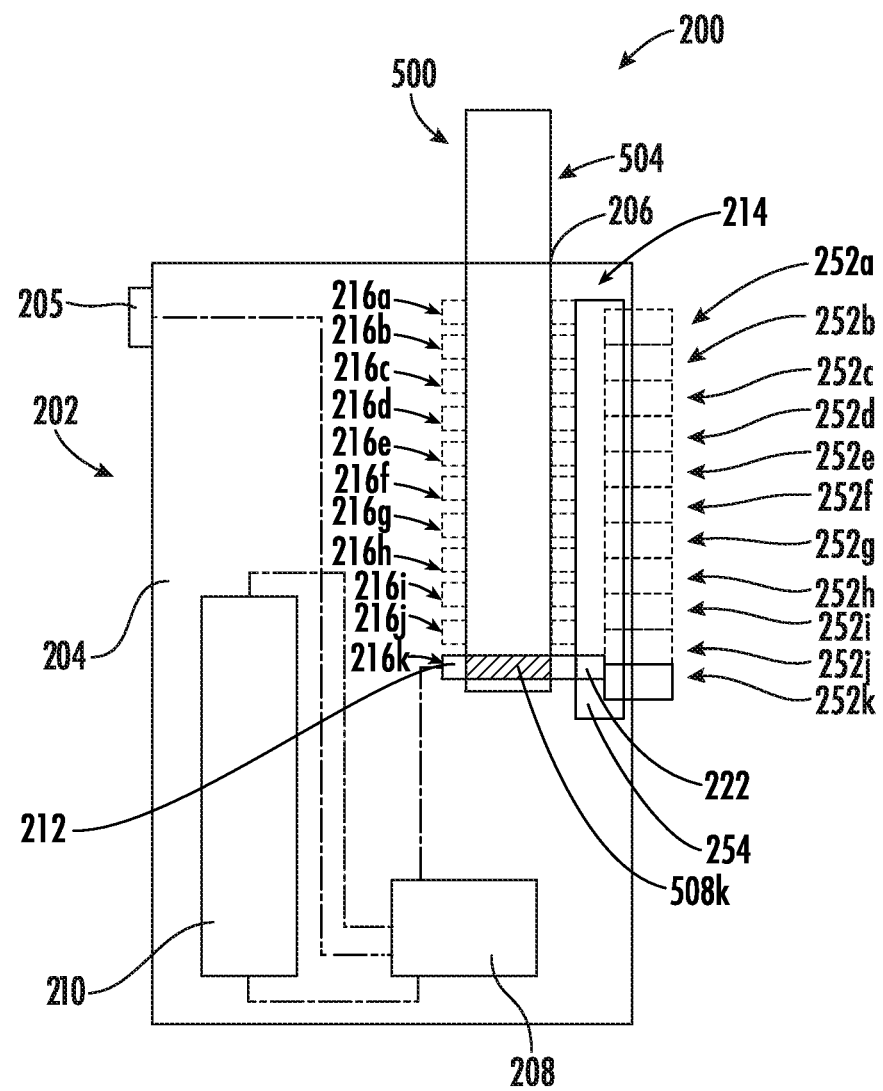
FIG. 6 schematically illustrates the aerosol delivery device of FIG. 4 showing a series of incremental heating positions, in accordance with an example implementation of the present disclosure.

In other implementations, the indexing of the heating member may be manually controlled by a consumer such that the heating member may be manually advanced by the consumer. For example, a schematic illustration of another example implementation of an aerosol delivery device 200 in accordance with the present disclosure is shown in FIGS. 4-6. In general, the aerosol delivery device 200 includes a control body 202 that includes a housing 204 configured to receive an aerosol source member 500. The housing may also include a pushbutton 205 configured to activate certain operations of the device 200, such as, for example, turning on the device and initiating heating of a heating member. In various implementations, the aerosol source member 500 may comprise a heated end 502, which is configured to be inserted into the control body 202, and a mouth end 504, upon which a user draws to create the aerosol. It should be noted that while the aerosol delivery device of FIGS. 4-6 is shown as having a substantially rectangular or fob-shaped control body 202 for ease of illustration, in other implementations the control body 202 may have an elongated shell or body that may be substantially tubular in shape and, as such, resemble the shape of a conventional cigarette or cigar, and thus the components described below may be sized and configured to fit inside an elongated body.

In various implementations, the control body 202 may be referred to as being reusable and the aerosol source member 500 may be referred to as being disposable. In some implementations, the entire device 200 may be characterized as being disposable in that the control body 202 may be configured for only a limited number of uses (e.g., until a battery power component no longer provides sufficient power to the article) with a limited number of aerosol source members 500 and, thereafter, the entire device 200, including the control body 202, may be discarded. In other implementations, the control body 202 may have a replaceable battery such that the control body 202 may be reused through a number of battery exchanges and with many aerosol source members 500. Similarly, the device 200 may be rechargeable and thus may be combined with any type of recharging technology, including connection to a typical electrical outlet, connection to a car charger (i.e., cigarette lighter receptacle), and connection to a computer, such as through a USB cable.

In various implementations, the housing 204 may be formed of any material suitable for forming and maintaining an appropriate conformation, such as a tubular or rectangular shape, and for retaining therein an aerosol source member. In some implementations, the housing may be formed of a single wall, or multiple walls, and from a material or multiple materials (natural or synthetic) that are heat resistant so as to retain its structural integrity—e.g., does not degrade—at least at a temperature that is the heating temperature provided by the electrical heating member, as discussed above. In some implementations, a heat resistant polymer may be used. In other implementations, ceramic materials may be used. In further implementations, an insulating material may be used so as not to unnecessarily move heat away from the aerosol source member. In some implementations, the size and shape of the housing may be similar to that described above with respect to FIGS. 1-3.

Although not depicted in the figures, the housing 204 may include one or more apertures therein for allowing entrance of ambient air to be directed into the heated end 502 of the aerosol source member 500. Thus, when a consumer draws on the mouth end 504 of the aerosol source member 500, air can be drawn into the receiving chamber, pass into the aerosol source member 500 proximate the heated end 502, and be drawn through the inhalable substance medium for inhalation by the consumer through the mouth end 504. In implementations wherein the overwrap is present, the drawn air may carry the inhalable substance through the optional filter and out of an opening of the overwrap.

In various implementations, the control body 202 may comprise an opening 206 defined in the housing 204, a flow sensor (not shown, e.g., a puff sensor or pressure switch), a control component 208 (e.g., a microprocessor, individually or as part of a microcontroller, a printed circuit board (PCB) that includes a microprocessor and/or microcontroller, etc.), and an electrical energy source 210 (e.g., a battery, which may be rechargeable, and/or a rechargeable supercapacitor). In some implementations, the control body 202 may also include a flow sensor (not shown, e.g., a puff sensor or pressure switch). Examples of power sources and other components that may be part of the aerosol delivery device 200 are described above with respect to FIGS. 1-3.

The aerosol delivery device 200 of the depicted implementation also includes a heating member 212, which receives power from the electrical energy source 210 and may be controlled by the control component 208. The heating member 212 may be any device suitable to provide heat sufficient to facilitate release of the inhalable substance for inhalation by a consumer. In certain implementations, the electrical heating member may be a resistance heating member. Useful heating members can be those having low mass, low density, and moderate resistivity and that are thermally stable at the temperatures experienced during use. Useful heating members heat and cool rapidly, and thus provide for the efficient use of energy. Rapid heating of the element also provides almost immediate volatilization of the aerosol-forming substance. Rapid cooling prevents substantial volatilization (and hence waste) of the aerosol-forming substance during periods when aerosol formation is not desired. Such heating members also permit relatively precise control of the temperature range experienced by the aerosol-forming substance, especially when time based current control is employed. Useful heating members also are chemically non-reactive with the materials comprising the inhalable substance medium being heated so as not to adversely affect the flavor or content of the aerosol or vapor that is produced. Example, non-limiting, materials that may comprise the heating member include carbon, graphite, carbon/graphite composites, metallic and non-metallic carbides, nitrides, silicides, inter-metallic compounds, cermets, metal alloys, and metal foils. In particular, refractory materials may be useful. Various, different materials can be mixed to achieve the desired properties of resistivity, mass, thermal conductivity, and surface properties.

As seen in FIGS. 4-6, the electrical heating member 212 of some implementations comprises a small segment heating member that may be in direct contact with the aerosol source member 500. Although in various implementations the structure of the heating member may vary, in some example implementations, the heating member may be a wire wound heating member, an etched foil heating member, or a heating member printed with inks on a temperature-resistant flexible film such as polyimide or silicone. Other depositing methodologies may also be used, including plasma deposition or chemical etching/deposition. In other implementations, the heating member may be a resistive metallic ribbon heater, or an infrared (optical) heater. Reference is also made to the description of the heating member 112 described above with respect to FIGS. 1-3. Direct contact may be preferred in light of the ability to provide conduction heating that is more rapid and that requires less resistance. In other implementations, however, the heating member may not be in contact with the inhalable substance medium, but, rather, may merely be proximate the inhalable substance medium. In some implementations, the heating member may have other shapes that correspond to the shape of the inhalable substance medium in the aerosol source member. Examples of heater arrays and possible heater configurations are described above with respect to FIGS. 1-3.

As noted above, the control body 202 may further include a control component 208. For example, the control component may comprise a control circuit (which may be connected to further components, as further described herein) that may be connected by electrically conductive wires to the electrical energy source 210. In various implementations, the control component may control when and how the heating member 212 receives electrical energy to heat the inhalable substance medium for release of the inhalable substance for inhalation by a consumer. Such control can relate to actuation of pressure sensitive switches or the like, which are described in greater detail hereinafter. The control component may also be configured to closely control the amount of heat provided to the inhalable substance medium and is described in more detail above with respect to FIGS. 1-3.

The aerosol delivery device 200 of the depicted implementation further includes an indexing mechanism 214 that includes an actuator 250, which, in some implementations, may be a thumb lever or the like. In various implementations, the indexing mechanism may be coupled to the heating member 212 and may be configured to generate incremental relative motion between the heating member 212 and the aerosol source member 500. In the depicted implementation, the indexing mechanism 214 is coupled to the heating member 212 such that the indexing mechanism 214 moves the heating member 212 through a series of incremental heating positions so as to incrementally heat a corresponding series of segments of the aerosol source member. In the depicted implementation, the actuator 250 is a manual mechanical actuator that is configured to move with the heating member 212 to position the heating member 212 in the plurality of heating positions.

In particular, in FIG. 4, the heating member 212 is shown in a first position 216*a* that is configured to heat a first segment 508*a* of the aerosol source member 500. FIG. 5 schematically illustrates the aerosol delivery device 200 of FIG. 4 showing the heating member 212 in a second heating position 216*b* in accordance with an example implementation of the present disclosure. The second position 216*b* is configured to heat a second segment 508*b* of the aerosol source member. As shown in the figure, in order to move the heating member 212 from the first heating position 216*a* to the second heating position 216*b*, the actuator 250 moves from a first actuator position 252*a* to a second actuator position 252*b*. FIG. 6 schematically illustrates the aerosol delivery device 200 of FIG. 4 showing a series of incremental heating positions 216*a-k* in accordance with an example implementation of the present disclosure. It should be noted that while the size and spacing of the heating positions in FIGS. 4-6 are depicted as such for clarity, as noted above, in various implementations the size and spacing of the heating positions may vary.

In the depicted implementation, the heating member 212 comprises a ring-like structure configured to surround a portion of an outside diameter of the aerosol source member 500. Such a structure may be formed of any suitable material, as described above, and preferably exhibits properties, such as described above. In the depicted implementation, the indexing mechanism 214 comprises a carrier 222, to which the heating member 212 is affixed, and a guide mechanism 254, through which the actuator 250 is configured to travel. In various implementations, the guide mechanism 254 may include a plurality of stopping points, detents, or other features configured to capture the actuator 250 at particular locations, and which are spaced linearly so as to correspond with the plurality of actuator positions 252. In such a manner, a consumer may move the actuator 250 linearly through the plurality of actuator positions 252 in order to progress the heating member 212 linearly through the plurality of heating positions. In various implementations, the characteristics (including for example, the dimensions and/or specifications and/or features) of the actuator and guide mechanism may be designed in order to meet a variety of performance objectives. For example, in the implementation depicted in FIGS. 4-6, the indexing mechanism 214 is configured such that the heating member 212 may be moved through a series of discrete linear positions 216. Because the aerosol source member 500 of the depicted implementation is stationary, these linear positions 216 correspond to a series of discrete segments 508 of the aerosol source member 500. As such, the control component 208, the carrier 222, the guide mechanism 254, and the actuator 250 are configured such that the heating member 212 may sequentially heat segments of the aerosol source member. Referring to FIG. 6, these segments are illustrated as segments 508*a-k*. It should be noted that, for purposes of clear illustration, the depicted implementation shows a total of eleven discrete positions 216*a-k* of the heating member 212, corresponding to eleven discrete heated segments 508a-k of the aerosol source member 500, however, in various other implementations the heating member may have any number of discrete positions corresponding to any number of discrete segments of the aerosol source member, including an infinite number thereof. Further, while the implementation depicted in FIGS. 4-6 shows a plurality of discrete heating member positions and corresponding discrete heating segments that are spaced apart from each other, in other implementations the discrete positions and corresponding discrete segments may have different spacing, including, but not limited to, spacing that results in the discrete positions and corresponding discrete segments abutting each other and/or overlapping each other, as well as inconsistent spacing.

In various implementations, movement of the heating member 212 may be initiated by the consumer via the actuator 250. For example, the consumer may advance the heating member 212 after a puffing action, or when prompted by the device 200 to do so. Thus, in some implementations, the consumer may determine when to advance the actuator 250, while in other implementations, the device 200 may provide an indication (such as, for example, through a sound and/or an indicator light) that the heating member 212 should be advanced. For example, in one implementation the user may advance the heating element 212 to the next position prior to taking a new draw on the aerosol source member 500. The heating element 212 will then be preheated to first temperature, T1. Once the segment has reached T1 (or a predetermined amount of time has elapsed), then the device 200 will indicate with a light or a sound that it is OK for the user to take a draw. In some implementations, the number of heating member positions 216 may correspond to the number of puffs available from the aerosol source member 500. In some implementations, a single aerosol source member may provide about 4 to about 12, about 5 to about 11, or about 6 to about 10 puffs, which approximates the number of puffs in a typical cigarette. In some implementations, once the heating member 212 has traveled through all of the available positions 216, the device may provide an indication (such as, for example, through a sound and/or an indicator light) that the heating member 212 has traveled through all of the available positions. In such a manner, the consumer may then move the actuator 250 back to the initial actuator position 252a. In some implementations, the aerosol source member 500 may be ejected when the actuator 250 is returned to the initial actuator position 252a. Although in various implementations the aerosol source member may be ejected in a variety of ways, in one implementation, reference is made to the method of ejection described above with respect to FIGS. 1-3.

Although across implementations operation of an aerosol delivery device may vary, in the example implementation of FIGS. 4-6, the general operation of the aerosol delivery device 200 may occur as follows, with one or more of the following steps occurring via control from the control component 208. In a first step, the heating member 212 may be turned on by pressing the pushbutton 205. In a second step, the user may click the actuator 250 downward, which may move the heating member 212 one linear position 216 (such as, for example, from a null position to a first position 216a) and cause the heating member 212 to pre-heat to a first temperature, T1. In a third step, the user may draw on the aerosol source member 500 (detected, for example, by a flow sensor), and the heating member 212 may heat to a second temperature, T2. When the user stops puffing (detected, for example, by a flow sensor), the heater may turn off. The user may then click the actuator 250 downward, which may move the heating member 212 to the next linear position 216 (such as, for example, position 216b) and cause the heating member 212 to pre-heat to a first temperature, T1. This process may continue until the heating member 212 travels to the last of the heating positions 216 (such as, for example, position 216k). At this point, the actuator 250 may be returned to its initial position and the aerosol source member 500 may be ejected from the housing 202.

Figure 7:
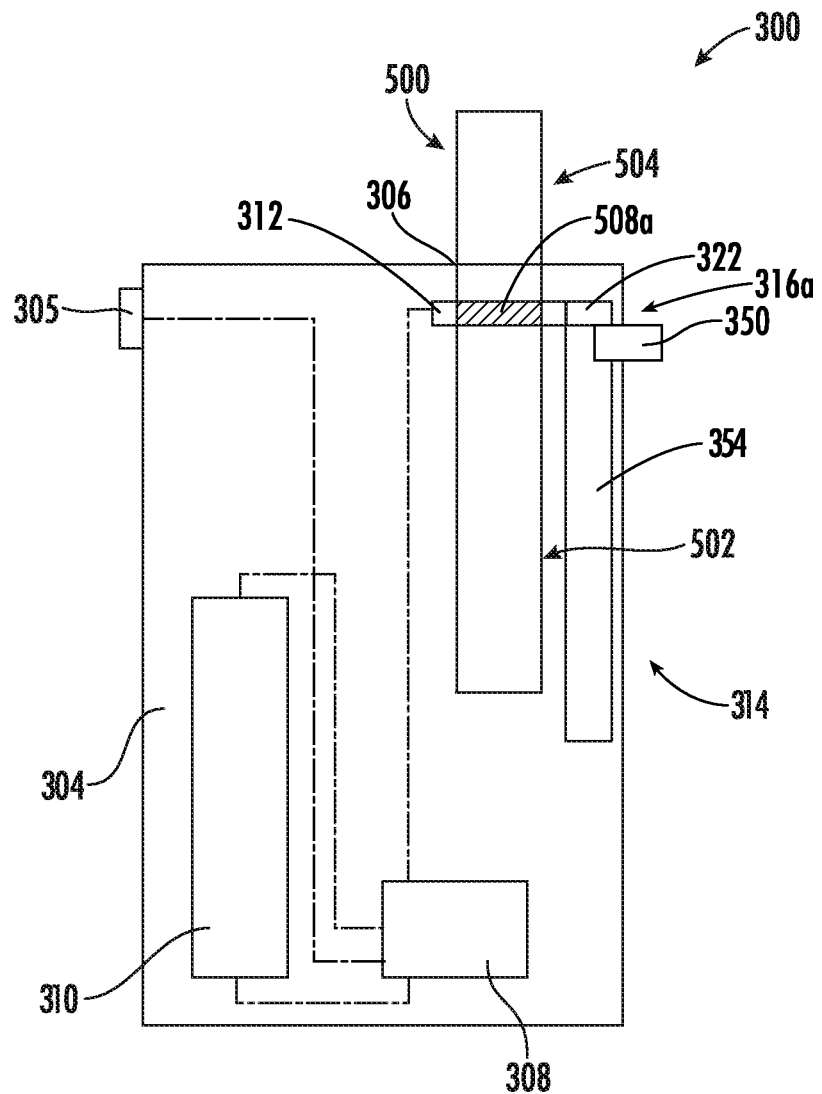
FIG. 7 schematically illustrates an aerosol delivery device including a heating member in a first heating position, in accordance with an example implementation of the present disclosure.
Figure 8:
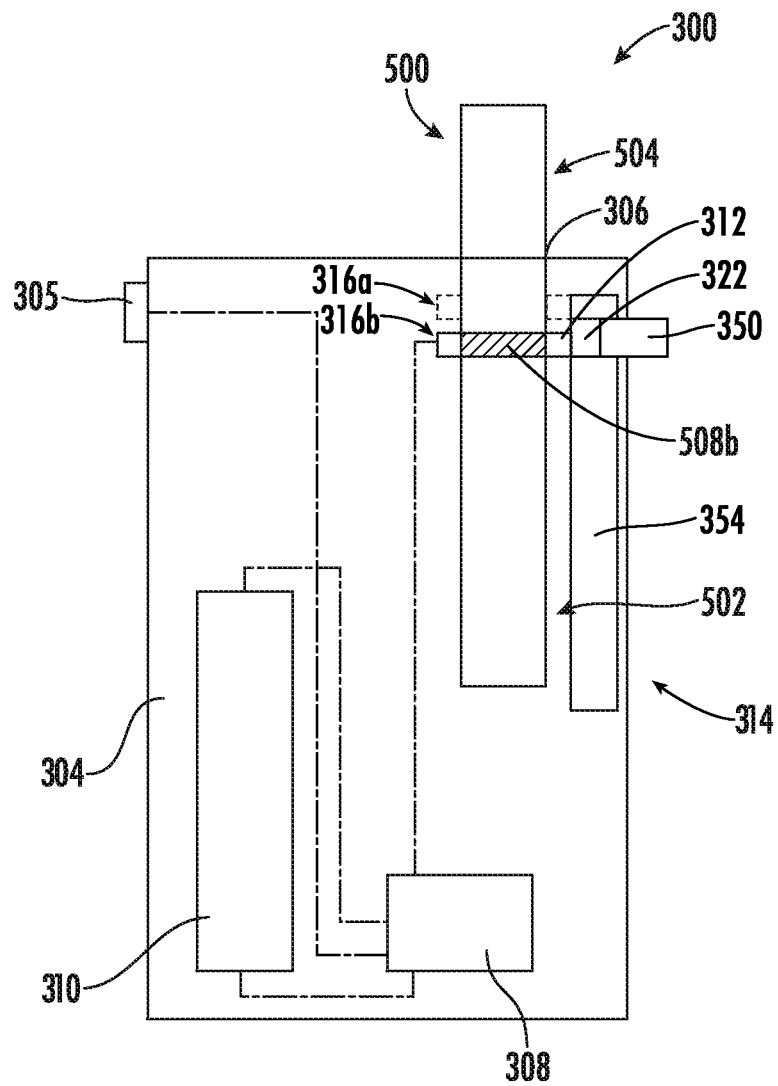
FIG. 8 schematically illustrates the aerosol delivery device of FIG. 7 showing the heating member in a second heating position, in accordance with an example implementation of the present disclosure.
Figure 9:
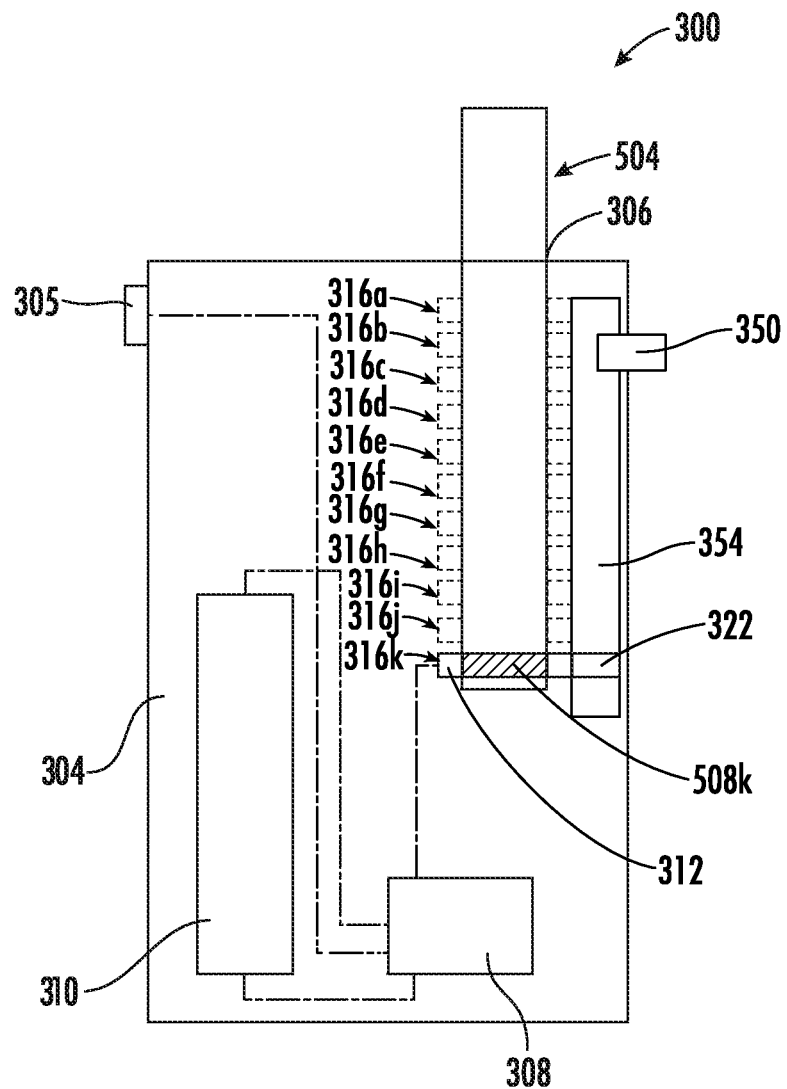
FIG. 9 schematically illustrates the aerosol delivery device of FIG. 7 showing a series of incremental heating positions, in accordance with an example implementation of the present disclosure.

A schematic illustration of another example implementation of an aerosol delivery device 300 in accordance with the present disclosure is shown in FIGS. 7-9. In general, the aerosol delivery device 300 includes a control body 302 that includes a housing 304 configured to receive an aerosol source member 500. The housing may also include a pushbutton 305 configured to activate certain operations of the device 300, such as, for example, turning on the device and initiating heating of a heating member. In various implementations, the aerosol source member 500 may comprise a heated end 502, which is configured to be inserted into the control body 302, and a mouth end 504, upon which a user draws to create the aerosol. It should be noted that while the aerosol delivery device of FIGS. 7-9 is shown as having a substantially rectangular or fob-shaped control body 302 for ease of illustration, in other implementations the control body 302 may have an elongated shell or body that may be substantially tubular in shape and, as such, resemble the shape of a conventional cigarette or cigar, and thus the components described below may be sized and configured to fit inside an elongated body.

In various implementations, the control body 302 may be referred to as being reusable and the aerosol source member 500 may be referred to as being disposable. In some implementations, the entire device 300 may be characterized as being disposable in that the control body 302 may be configured for only a limited number of uses (e.g., until a battery power component no longer provides sufficient power to the article) with a limited number of aerosol source members 500 and, thereafter, the entire device 300, including the control body 302, may be discarded. In other implementations, the control body 302 may have a replaceable battery such that the control body 302 may be reused through a number of battery exchanges and with many aerosol source members 500. Similarly, the device 300 may be rechargeable and thus may be combined with any type of recharging technology, including connection to a typical electrical outlet, connection to a car charger (i.e., cigarette lighter receptacle), and connection to a computer, such as through a USB cable.

In various implementations, the housing 304 may be formed of any material suitable for forming and maintaining an appropriate conformation, such as a tubular or rectangular shape, and for retaining therein an aerosol source member. In some implementations, the housing may be formed of a single wall, or multiple walls, and from a material or multiple materials (natural or synthetic) that are heat resistant so as to retain its structural integrity—e.g., does not degrade—at least at a temperature that is the heating temperature provided by the electrical heating member, as discussed above. In some implementations, a heat resistant polymer may be used. In other implementations, ceramic materials may be used. In further implementations, an insulating material may be used so as not to unnecessarily move heat away from the aerosol source member. The size and shape of the housing may be similar to that described above with respect to FIGS. 1-3.

Although not depicted in the figures, the housing 304 may include one or more apertures therein for allowing entrance of ambient air to be directed into the heated end 502 of the aerosol source member 500. Thus, when a consumer draws on the mouth end 504 of the aerosol source member 500, air can be drawn into the receiving chamber, pass into the aerosol source member 500 proximate the heated end 502, and be drawn through the inhalable substance medium for inhalation by the consumer through the mouth end 504. In implementations wherein the overwrap is present, the drawn air may carry the inhalable substance through the optional filter and out of an opening of the overwrap.

The control body 302 may comprise an opening 306 defined therein, a control component 308 (e.g., a microprocessor, individually or as part of a microcontroller, a printed circuit board (PCB) that includes a microprocessor and/or microcontroller, etc.), and an electrical energy source 310 (e.g., a battery, which may be rechargeable, and/or a rechargeable supercapacitor). In some implementations, the control body 302 may also include a flow sensor (not shown, e.g., a puff sensor or pressure switch). Examples of power sources and other components that may be part of the aerosol delivery device 300 are described above with respect to FIGS. 1-3.

The aerosol delivery device 300 of the depicted implementation also includes a heating member 312, which receives power from the electrical energy source 310 and may be controlled by the control component 308. The heating member 312 may be any device suitable to provide heat sufficient to facilitate release of the inhalable substance for inhalation by a consumer. In certain implementations, the electrical heating member may be a resistance heating member. Useful heating members can be those having low mass, low density, and moderate resistivity and that are thermally stable at the temperatures experienced during use. Useful heating members heat and cool rapidly, and thus provide for the efficient use of energy. Rapid heating of the element also provides almost immediate volatilization of the aerosol-forming substance. Rapid cooling prevents substantial volatilization (and hence waste) of the aerosol-forming substance during periods when aerosol formation is not desired. Such heating members also permit relatively precise control of the temperature range experienced by the aerosol-forming substance, especially when time based current control is employed. Useful heating members also are chemically non-reactive with the materials comprising the inhalable substance medium being heated so as not to adversely affect the flavor or content of the aerosol or vapor that is produced. Example, non-limiting, materials that may comprise the heating member include carbon, graphite, carbon/graphite composites, metallic and non-metallic carbides, nitrides, silicides, inter-metallic compounds, cermets, metal alloys, and metal foils. In particular, refractory materials may be useful. Various, different materials can be mixed to achieve the desired properties of resistivity, mass, thermal conductivity, and surface properties.

As seen in FIGS. 7-9, the electrical heating member 312 of some implementations comprises a small segment heating member that may be in direct contact with the aerosol source member. Although in various implementations the structure of the heating member may vary, in some example implementations, the heating member may be a wire wound heating member, an etched foil heating member, or a heating member printed with inks on a temperature-resistant flexible film such as polyimide or silicone. Other depositing methodologies may also be used, including plasma deposition or chemical etching/deposition. In other implementations, the heating member may be a resistive metallic ribbon heater, or an infrared (optical) heater. Reference is also made to the description of the heating member 112 described above with respect to FIGS. 1-3. Direct contact may be preferred in light of the ability to provide conduction heating that is more rapid and that requires less resistance. In other implementations, however, the heating member may not be in contact with the inhalable substance medium, but, rather, may merely be proximate the inhalable substance medium. In some implementations, the heating member may have other shapes that correspond to the shape of the inhalable substance medium in the aerosol source member. Examples of heater arrays and possible heater configurations are described above with respect to FIGS. 1-3.

As noted above, the control body 302 may further include a control component 308. For example, the control component may comprise a control circuit (which may be connected to further components, as further described herein) that may be connected by electrically conductive wires to the electrical energy source 310. In various implementations, the control component 308 may control when and how the heating member 312 receives electrical energy to heat the inhalable substance medium for release of the inhalable substance for inhalation by a consumer. Such control can relate to actuation of pressure sensitive switches or the like, which are described in greater detail hereinafter. The control component may also be configured to closely control the amount of heat provided to the inhalable substance medium and is described in more detail above with respect to FIGS. 1-3.

The aerosol delivery device 300 of the depicted implementation further includes an indexing mechanism 314 that includes an actuator 350, which in some implementations may be a thumb lever or the like. In various implementations, the indexing mechanism 314 may be coupled to the heating member 312 and may be configured to generate incremental relative motion between the heating member 312 and the aerosol source member 500. In the depicted implementation, the indexing mechanism 314 is coupled to the heating member 312 such that the indexing mechanism 314 remains relatively stationary but is configured to move the heating member 312 through a series of incremental heating positions so as to incrementally heat a corresponding series of segments of the aerosol source member 500. As such, in the depicted implementation, the actuator 350 is a click-return actuator that advances the heating member one position with every actuation of the actuator 350.

In particular, in FIG. 7, the heating member 312 is shown in a first position 316*a* that is configured to heat a first segment 508*a* of the aerosol source member 500. FIG. 8 schematically illustrates the aerosol delivery device 300 of FIG. 7 showing the heating member 312 in a second heating position 316*b* in accordance with an example implementation of the present disclosure. The second position 316*b* is configured to heat a second segment 508*b* of the aerosol source member. As shown in the figure, in order to move the heating member 312 from the first heating position 316*a* to the second heating position 316*b*, the actuator 350 is pressed downward and returns to its original position. FIG. 9 schematically illustrates the aerosol delivery device 300 of FIG. 7 showing a series of incremental heating positions 316 *a-k* in accordance with an example implementation of the present disclosure. It should be noted that while the size and spacing of the heating positions in FIGS. 7-9 are depicted as such for clarity, as noted above, in various implementations the size and spacing of the heating positions may vary.

In various implementations, a variety of click-return mechanisms may be employed to advance the heating member 312 through the plurality of heating positions 316. Such mechanisms may include, but need not be limited to, ratchet mechanisms, Geneva mechanisms, sector gear mechanisms, Whitworth mechanisms, ratchet mechanisms, bell crank, slotted yoke, and cam-follower mechanisms, such as those used in small mechanical devices, (e.g., a ball point pen).

In the depicted implementation, the heating member 312 comprises a ring-like structure configured to surround a portion of an outside diameter of the aerosol source member 500. Such a structure may be formed of any suitable material, as described above, and preferably exhibits properties, such as described above. In the depicted implementation, the indexing mechanism 314 comprises a carrier 322, to which the heating member 312 is affixed, and a guide mechanism 354, configured to guide the carrier 322 and heating member 312 through the plurality of positions. In such a manner, a consumer may actuate the actuator 350, such as pressing the actuator 350 downward, which sequentially advances the heating member 312 linearly through the plurality of heating member positions. In various implementations, the characteristics (including for example, the dimensions and/or specifications and/or features) of the actuator and guide mechanism may be designed in order to meet a variety of performance objectives. For example, in the implementation depicted in FIGS. 7-9, the indexing mechanism 314 is configured such that the heating member 312 may be moved through a series of discrete linear positions 316. Because the aerosol source member 500 of the depicted implementation is stationary, these linear positions 316 correspond to a series of discrete segments 508 of the aerosol source member 500. As such, the carrier 322, guide mechanism 354, and actuator 350 are configured such that the heating member 312 may sequentially heat the segments of the aerosol source member. Referring to FIG. 9, these segments are illustrated as segments 508*a-k*. It should be noted that, for purposes of clear illustration, the depicted implementation shows a total of eleven discrete heating member positions 316 *a-k* corresponding to eleven discrete heating segments 508 *a-k* of the aerosol source member 500, however, in various other implementations the heating member may have any number of discrete positions corresponding to any number of discrete segments of the aerosol source member, including an infinite number thereof. Further, while the implementation depicted in FIGS. 7-9 shows a plurality of discrete heating member positions and corresponding discrete heating segments that are spaced apart from each other, in other implementations the discrete positions and corresponding discrete segments may have different spacing, including, but not limited to, spacing that results in the discrete positions and corresponding discrete segments abutting each other and/or overlapping each other, as well as inconsistent spacing.

In various implementations, movement of the heating member 312 may be initiated by the consumer via the actuator 350. For example, the consumer may advance the heating member 312 after a puffing action, or when prompted by the device 300 to do so. Thus, in some implementations, the consumer may determine when to advance the actuator, while in other implementations, the device 300 may provide an indication (such as, for example, through a sound and/or an indicator light) that the heating member should be advanced. In some implementations, the number of heating member positions 316 may correspond to the number of puffs available from the aerosol source member 500. In some implementations, a single aerosol source member may provide about 4 to about 12, about 5 to about 11, or about 6 to about 10 puffs, which approximates the number of puffs in a typical cigarette. In some implementations, once the heating member 312 has traveled through all of the available positions 316, the device may provide an indication (such as, for example, through a sound and/or an indicator light) that the heating member has traveled through all of the available positions. In such a manner, the consumer may move the actuator 350 in a different direction (e.g., upward) in order to return the heating member 312 back to its initial position. In addition, in some implementations, the aerosol source member 500 may be ejected when the actuator 350 is moved in a different direction.

Although operation of the device may vary, in one example implementation, the general operation of the aerosol delivery device 300 of FIGS. 7-9 may occur as follows, with one or more of the following steps occurring via control from the control component 308. In a first step, the heating member 312 may be turned on by pressing the pushbutton 305. In a second step, the user may click the actuator 350 downward, which may move the heating member 312 one linear position 316 (such as, for example, from a null position to a first position 316*a*) and cause the heating member 312 to pre-heat to a first temperature, T1. Due to the nature of the click-return mechanism, the actuator 350 may return to its original position. In a third step, the user may draw on the aerosol source member (detected, for example, by a flow sensor), and the heating member 312 may heat to a second temperature, T2. When the user stops puffing (detected, for example, by a flow sensor), the heater may turn off. The user may then click the actuator 350 downward, which may move the heating member 312 to the next linear position 316 (such as, for example, position 316*b*) and cause the heating member 312 to pre-heat to a first temperature, T1. Once again, due to the nature of the click-return mechanism, the actuator 350 may return to its original position. This process may continue until the heating member 312 travels to the last of the heating positions 316 (such as, for example, position 316*k*). At this point, the actuator 350 may be pressed in another direction, such as upward, in order to eject the aerosol source member 500 from the housing 302. Although in various implementations the aerosol source member may be ejected in a variety of ways, in one implementation, reference is made to the method of ejection described above with respect to FIGS. 1-3.

Figure 10:
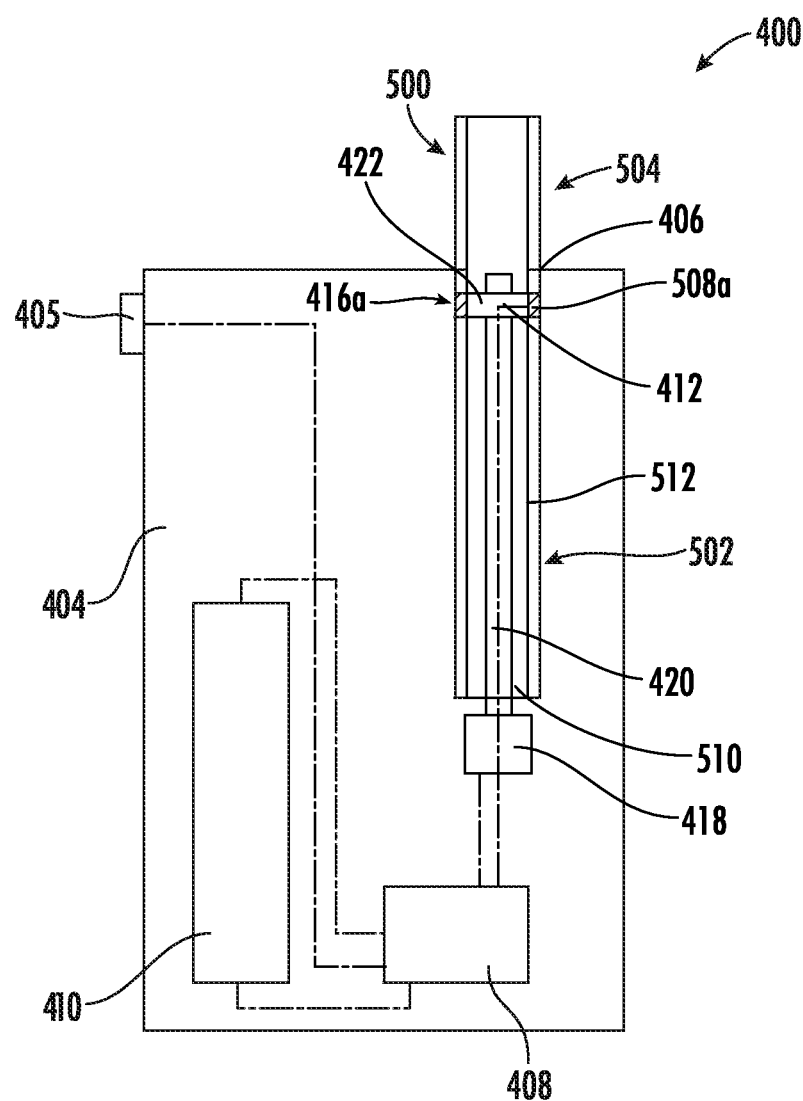
FIG. 10 schematically illustrates an aerosol delivery device including a heating member in a first heating position, in accordance with an example implementation of the present disclosure.
Figure 11:
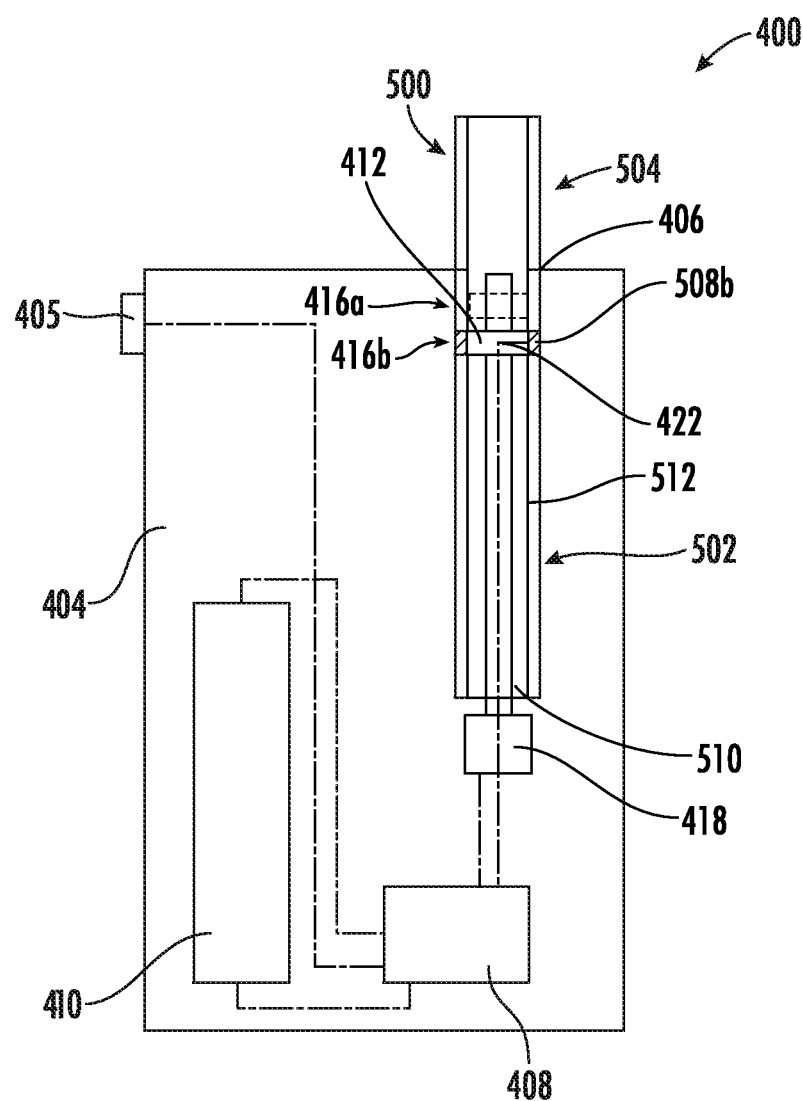
FIG. 11 schematically illustrates the aerosol delivery device of FIG. 10 showing the heating member in a second heating position, in accordance with an example implementation of the present disclosure.
Figure 12:
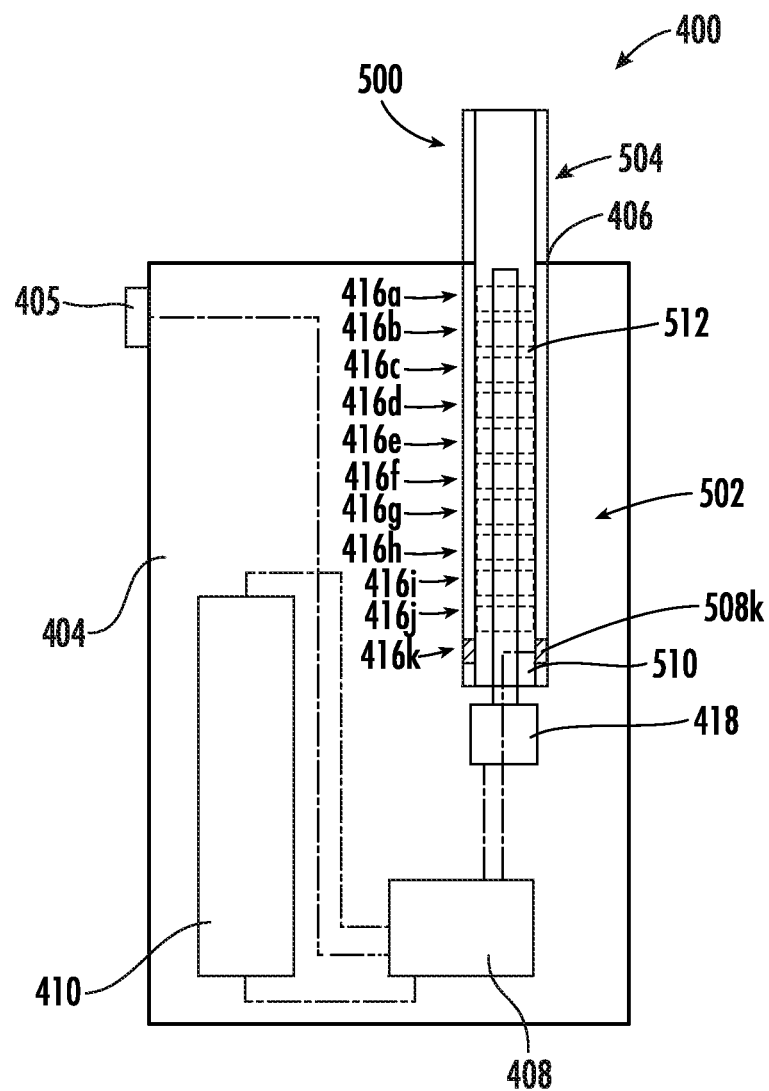
FIG. 12 schematically illustrates the aerosol delivery device of FIG. 10 showing a series of incremental heating positions, in accordance with an example implementation of the present disclosure.

A schematic illustration of another example implementation of an aerosol delivery device 400 in accordance with the present disclosure is shown in FIGS. 10-12. In general, the aerosol delivery device 400 includes a control body 402 that includes a housing 404 configured to receive an aerosol source member 500. The housing may also include a pushbutton 405 configured to activate certain operations of the device 400, such as, for example, turning on the device and initiating heating of a heating member. In various implementations, the aerosol source member 500 may comprise a heated end 502, which is configured to be inserted into the control body 402, and a mouth end 504, upon which a user draws to create the aerosol. It should be noted that while the aerosol delivery device of FIGS. 10-12 is shown as having a substantially rectangular or fob-shaped control body 402 for ease of illustration, in other implementations the control body 402 may have an elongated shell or body that may be substantially tubular in shape and, as such, resemble the shape of a conventional cigarette or cigar, and thus the components described below may be sized and configured to fit inside an elongated body.

In various implementations, the control body 402 may be referred to as being reusable, and the aerosol source member 500 may be referred to as being disposable. In some implementations, the entire device 400 may be characterized as being disposable in that the control body 402 may be configured for only a limited number of uses (e.g., until a battery power component no longer provides sufficient power to the article) with a limited number of aerosol source members 500 and, thereafter, the entire device 400, including the control body 402, may be discarded. In other implementations, the control body 402 may have a replaceable battery such that the control body 402 may be reused through a number of battery exchanges and with many aerosol source members 500. Similarly, the device 400 may be rechargeable and thus may be combined with any type of recharging technology, including connection to a typical electrical outlet, connection to a car charger (i.e., cigarette lighter receptacle), and connection to a computer, such as through a USB cable, or connection to a wireless charger, such as a charger that uses inductive wireless charging (including for example, wireless charging according to the Qi wireless charging standard from the Wireless Power Consortium (WPC)), or a wireless radio frequency (RF) based charger.

In various implementations, the housing 404 may be formed of any material suitable for forming and maintaining an appropriate conformation, such as a tubular or rectangular shape, and for retaining therein an aerosol source member. In some implementations, the housing may be formed of a single wall, or multiple walls, and from a material or multiple materials (natural or synthetic) that are heat resistant so as to retain its structural integrity—e.g., does not degrade—at least at a temperature that is the heating temperature provided by the electrical heating member, as further discussed herein. In some implementations, a heat resistant polymer may be used. In other implementations, ceramic materials may be used. In further implementations, an insulating material may be used so as not to unnecessarily move heat away from the aerosol source member. The size and shape of the housing may be similar to that described above with respect to FIGS. 1-3.

Although not depicted in the figures, the housing 404 may include one or more apertures therein for allowing entrance of ambient air to be directed into the heated end 502 of the aerosol source member 500. Thus, when a consumer draws on the mouth end 504 of the aerosol source member 500, air can be drawn into the receiving chamber, pass into the aerosol source member 500 proximate the heated end 502, and be drawn through the inhalable substance medium for inhalation by the consumer through the mouth end 504. In implementations wherein the overwrap is present, the drawn air may carry the inhalable substance through the optional filter and out of an opening of the overwrap.

The control body 402 may comprise an opening 406 defined therein, a control component 408 (e.g., a microprocessor, individually or as part of a microcontroller, a printed circuit board (PCB) that includes a microprocessor and/or microcontroller, etc.), and an electrical energy source 410 (e.g., a battery, which may be rechargeable, and/or a rechargeable supercapacitor). In some implementations, the control body 402 may also include a flow sensor (not shown, e.g., a puff sensor or pressure switch). Examples of power sources and other components that may be part of the aerosol delivery device 400 are described above with respect to FIGS. 1-3.

The aerosol delivery device 400 of the depicted implementation also includes a heating member 412, which receives power from the electrical energy source 410 and may be controlled by the control component 408. The heating member 412 may be any device suitable to provide heat sufficient to facilitate release of the inhalable substance for inhalation by a consumer. In certain implementations, the electrical heating member may be a resistance heating member. Useful heating members can be those having low mass, low density, and moderate resistivity and that are thermally stable at the temperatures experienced during use. Useful heating members heat and cool rapidly, and thus provide for the efficient use of energy. Rapid heating of the element also provides almost immediate volatilization of the aerosol-forming substance. Rapid cooling prevents substantial volatilization (and hence waste) of the aerosol-forming substance during periods when aerosol formation is not desired. Such heating members also permit relatively precise control of the temperature range experienced by the aerosol-forming substance, especially when time based current control is employed. Useful heating members also are chemically non-reactive with the materials comprising the inhalable substance medium being heated so as not to adversely affect the flavor or content of the aerosol or vapor that is produced. Example, non-limiting, materials that may comprise the heating member include carbon, graphite, carbon/graphite composites, metallic and non-metallic carbides, nitrides, silicides, inter-metallic compounds, cermets, metal alloys, and metal foils. In particular, refractory materials may be useful. Various, different materials can be mixed to achieve the desired properties of resistivity, mass, thermal conductivity, and surface properties.

As seen in FIGS. 10-12, the electrical heating member 412 of some implementations comprises a small segment heating member that may be in direct contact with the aerosol source member 500. Although in various implementations the structure of the heating member may vary, in some example implementations, the heating member may be a wire wound heating member, an etched foil heating member, or a heating member printed with inks on a temperature-resistant flexible film such as polyimide or silicone. Other depositing methodologies may also be used, including plasma deposition or chemical etching/deposition. In other implementations, the heating member may be a resistive metallic ribbon heater, or an infrared (optical) heater. Reference is also made to the description of the heating member 112 described above with respect to FIGS. 1-3. Direct contact may be preferred in light of the ability to provide conduction heating that is more rapid and that requires less resistance. In other implementations, however, the heating member may not be in contact with the inhalable substance medium, but, rather, may merely be proximate the inhalable substance medium. In other implementations, the heating member may have other shapes that correspond to the shape of the inhalable substance medium in the aerosol source member. Examples of heater arrays and possible heater configurations are described above with respect to FIGS. 1-3.

As noted above, the control body 402 may further include a control component 408. For example, the control component may comprise a control circuit (which may be connected to further components, as further described herein) that may be connected by electrically conductive wires to the electrical energy source 410. In various implementations, the control component may control when and how the heating member 412 receives electrical energy to heat the inhalable substance medium for release of the inhalable substance for inhalation by a consumer. Such control can relate to actuation of pressure sensitive switches or the like, which are described in greater detail hereinafter. The control component may also be configured to closely control the amount of heat provided to the inhalable substance medium and is described in more detail above with respect to FIGS. 1-3.

The aerosol delivery device 400 of the depicted implementation further includes an indexing mechanism 414. In various implementations, the indexing mechanism 414 may be coupled to the heating member 412 and may be configured to generate incremental relative motion between the heating member 412 and the aerosol source member 500. In the depicted implementation, the indexing mechanism 414 is coupled to the heating member 412 such that indexing mechanism 414 moves the heating member 412 through a series of incremental heating positions so as to incrementally heat a corresponding series of segments of the aerosol source member 500. In particular, in FIG. 10, the heating member 412 is shown in a first position 416a that is configured to heat a first segment 508a of the aerosol source member 500. FIG. 11 schematically illustrates the aerosol delivery device 400 of FIG. 10 showing the heating member 412 in a second heating position 416b in accordance with an example implementation of the present disclosure. The second position 416b is configured to heat a second segment 508b of the aerosol source member 500. FIG. 12 schematically illustrates the aerosol delivery device 400 of FIG. 10 showing a series of incremental heating positions 416 a-k in accordance with an example implementation of the present disclosure. It should be noted that while the size and spacing of the heating positions in FIGS. 10-12 are depicted as such for clarity, as noted above, in various implementations the size and spacing of the heating positions may vary.

In the depicted implementation, the aerosol source member 500 has an extruded tube-shape, and the heating member 412 comprises a disc-like structure configured to fit within a cavity 510 defined by an internal surface 512 of the aerosol source member 500. In other implementations, the aerosol source member and the heating member may have other shapes. For example, in some implementations, the aerosol source member may have any hollow shape. In some implementations, the heating member may have any shape, including, for example, a shape that is complementary to a shape of an interior portion of an aerosol source member. In the depicted implementation, the indexing mechanism 414 comprises a small motor 418 (e.g., a micro stepping motor) configured to rotate a lead screw 420. A carrier 422, to which the heating member 412 is affixed, may be threaded through the lead screw 420. In such a manner, rotation of the lead screw 420 by the stepper motor 418 may therefor move the carrier 422, and thus the heating member 412, in a substantially linear fashion. In various implementations, the characteristics (including for example, the dimensions and/or specifications and/or control features) of the control component, stepper motor, lead screw, and carrier may be designed in order to meet a variety of performance objectives. For example, in the implementation depicted in FIGS. 10-12, the indexing mechanism 414 is configured such that the heating member 412 may be moved through a series of discrete linear positions 416. Because the aerosol source member 500 of the depicted implementation is stationary, these linear positions 416 correspond to a series of discrete segments 508 of the aerosol source member 500. As such, the control component 408, stepper motor 418, lead screw 420, carrier 422, and heating member 412 are configured such that the heating member 412 may sequentially heat the segments of the aerosol source member. Referring to FIG. 12, these segments are illustrated as segments 508 a-k. It should be noted that, for purposes of clear illustration, the depicted implementation shows a total of eleven discrete heating member positions 416 a-k corresponding to eleven discrete heating segments 508 a-k of the aerosol source member 500, however, in various other implementations the heating member may have any number of discrete positions corresponding to any number of discrete segments of the aerosol source member, including an infinite number thereof. Further, while the implementation depicted in FIGS. 10-12 shows a plurality of discrete positions and corresponding discrete heating member segments that are spaced apart from each other, in other implementations the discrete positions and corresponding discrete segments may have different spacing, including, but not limited to, spacing that results in the discrete positions and corresponding discrete segments abutting each other and/or overlapping each other, as well as inconsistent spacing.

In various implementations, movement of the heating member 412 may be initiated by the puffing action of the consumer through use of one or more various sensors, as otherwise described herein, and/or may be initiated once the puff is discontinued as sensed by one or more various sensors. Thus, in some implementations, the number of heating member positions 416 may correspond to the number of puffs available from the aerosol source member 500. In some implementations, a single aerosol source member may provide about 4 to about 12, about 5 to about 11, or about 6 to about 10 puffs, which approximates the number of puffs in a typical cigarette. In some implementations, once the heating member 412 has traveled through all of the available positions 416, the motor 418 may reverse direction and return the carrier 422 and heating member 412 to its first or starting position. In other implementations, the heating member 412 may remain at its last or final position or may be positioned at any other position or a location in between. In addition, in some implementations the controller may provide an indication (such as, for example, through a sound and/or indicator light) that the heating member has traveled through all of the available positions 416. In some implementations, the aerosol source member 500 may be ejected when the heating member has traveled through all of the available positions 416.

Although operation of the device may vary, in one example implementation, the general operation of the aerosol delivery device 400 of FIGS. 10-12 may occur as follows, with one or more of the following steps occurring via control from the control component 408. In a first step, the heating member 412, located at a first heating position 416 (such as, for example, position 416a), may be turned on by pressing the pushbutton 405. In addition, the heating member 412 may pre-heat to a first temperature, T1. In a second step, the user may draw on the aerosol source member (detected, for example, by a flow sensor), and the heating member 412 may heat to a second temperature, T2. When the user stops puffing (detected, for example, by a flow sensor), the heater temperature may return to the first temperature, T1, and the indexing mechanism 414 may automatically move the next heating position 416 (such as, for example, position 416b). This process may continue until the heating member 412 travels to the last of the heating positions 416 (such as, for example, position 416k). After this point, the aerosol source member 500 may be ejected from the housing 402. Although in various implementations the aerosol source member may be ejected in a variety of ways, in one implementation, reference is made to the method of ejection described above with respect to FIGS. 1-3.

It should be noted that instead of (or in addition to) any of the pushbuttons of the various implementations described above, the aerosol delivery device may include components that energize the heating member in response to other considerations, such as the consumer's drawing on the article (i.e., puff-actuated heating). As noted, the article may include a switch in the control component that is sensitive either to pressure changes or air flow changes as the consumer draws on the article (i.e., a puff-actuated switch). Other suitable current actuation/deactuation mechanisms may include a temperature actuated on/off switch or a lip pressure actuated switch. An example mechanism that can provide such puff-actuation capability includes a Model 163PC01D36 silicon sensor, manufactured by the Micro-Switch division of Honeywell, Inc., Freeport, Ill. With such a sensor, the heating member may be activated rapidly by a change in pressure when the consumer draws on the article. In addition, flow sensing devices, such as those using hot-wire anemometry principles, may be used to cause the energizing of the heating member sufficiently rapidly after sensing a change in air flow. A further puff actuated switch that may be used is a pressure differential switch, such as Model No. MPL-502-V, range A, from Micro Pneumatic Logic, Inc., Ft. Lauderdale, Fla. Another suitable puff actuated mechanism is a sensitive pressure transducer (e.g., equipped with an amplifier or gain stage) which is in turn coupled with a comparator for detecting a predetermined threshold pressure. Yet another suitable puff actuated mechanism is a vane which is deflected by airflow, the motion of which vane is detected by a movement sensing means. Yet another suitable actuation mechanism is a piezoelectric switch. Also useful is a suitably connected Honeywell MicroSwitch Microbridge Airflow Sensor, Part No. AWM 2100V from MicroSwitch Division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Other suitable differential switches, analog pressure sensors, flow rate sensors, or the like, will be apparent to the skilled artisan with the knowledge of the present disclosure. A pressure-sensing tube or other passage providing fluid connection between the puff actuated switch and the heated end of aerosol source member preferably may be included in the control body so that pressure changes during draw are readily identified by the switch.

In some implementations, when the consumer draws on the mouth end of the aerosol source member, current actuation means may permit unrestricted or uninterrupted flow of current through the heating member to generate heat rapidly. Because of the rapid heating, it can be useful to include current regulating components to (i) regulate current flow through the heating member to control heating of the resistance element and the temperature experienced thereby, and (ii) prevent overheating and degradation of the inhalable substance medium.

In some implementations, the current regulating circuit particularly may be time-based. Specifically, such a circuit may include a means for permitting uninterrupted current flow through the heating member for an initial time period during draw, and a timer means for subsequently regulating current flow until draw is completed. For example, the subsequent regulation can include the rapid on-off switching of current flow (e.g., on the order of about every 1 to 50 milliseconds) to maintain the heating member within a desired temperature range. Further, regulation may comprise simply allowing uninterrupted current flow until the desired temperature is achieved then turning off the current flow completely. The heating member may be reactivated by the consumer initiating another puff on the article (or manually actuating the pushbutton, depending upon the specific switch implementation employed for activating the heater). Alternatively, the subsequent regulation may involve the modulation of current flow through the heating member to maintain the heating member within a desired temperature range. In some implementations, so as to release the desired dosing of the inhalable substance, the heating member may be energized for a duration of about 0.2 second to about 5.0 seconds, about 0.3 second to about 4.0 seconds, about 0.4 second to about 3.0 seconds, about 0.5 second to about 2.0 seconds, or about 0.6 second to about 1.5 seconds. One example time-based current regulating circuit can include a transistor, a timer, a comparator, and a capacitor. Suitable transistors, timers, comparators, and capacitors are commercially available and will be apparent to the skilled artisan. Example timers are those available from NEC Electronics as C-1555C and from General Electric Intersil, Inc. as ICM7555, as well as various other sizes and configurations of so-called "555 Timers". An example comparator is available from National Semiconductor as LM311. Further description of such time-based current regulating circuits is provided in U.S. Pat. No. 4,947,874 to Brooks et al., which is incorporated herein by reference in its entirety. In some implementations, the heater control scheme may include closed-loop temperature control of the heating member. In such a case, the heating member temperature may be sensed and provided to the controller. For example, heater temperature control may be provided by including a sensor such as a thermistor or thermocouple in close proximity to the heating member/substrate interface and/or by monitoring the resistance of the heating member itself and utilizing the known relationship between temperature and resistivity of the particular heating member alloy to infer the heating member temperature.

In light of the foregoing, it can be seen that a variety of mechanisms may be employed to facilitate actuation/deactuation of current to the heating member. For example, the aerosol delivery device may comprise a timer for regulating current flow in the article (such as during draw by a consumer). The article may further comprise a timer responsive switch that enables and disables current flow to the heating member. Current flow regulation may also comprise use of a capacitor and components for charging and discharging the capacitor at a defined rate (e.g., a rate that approximates a rate at which the heating member heats and cools). Current flow may specifically be regulated such that there is uninterrupted current flow through the heating member for an initial time period during draw, but the current flow may be turned off or cycled alternately off and on after the initial time period until draw is completed. Such cycling may be controlled by a timer, as discussed above, which may generate a preset switching cycle. In some implementations, the timer may generate a periodic digital wave form. The flow during the initial time period further may be regulated by use of a comparator that compares a first voltage at a first input to a threshold voltage at a threshold input and generates an output signal when the first voltage is equal to the threshold voltage, which enables the timer. Such implementations may further include components for generating the threshold voltage at the threshold input and components for generating the threshold voltage at the first input upon passage of the initial time period.

In further implementations, puff actuation of the heating member may be coupled to movement of the heating member. For example, the current regulating component may allow the heating member to rapidly achieve the desired temperature and then remain at that temperature for the duration of the puff by the consumer. Further, in some implementations, puff actuated movement of the heating member may be continuous for the duration of the puff. Once the puff ceases, the heating member may be deactivated and cease movement. Thus, in some implementations, the distance traveled by the heating member during automatic indexing may be directly related to the duration of a puff. In this manner, the consumer may have control over the amount of the inhalable substance that is delivered by a single puff. A short puff may only deliver a small amount of the inhalable substance, while a longer puff may deliver a greater amount of the inhalable substance. Thus, a large, initial puff may provide a bolus of the inhalable substance, and shorter puffs thereafter may provide smaller amounts of the inhalable substance. Example puff actuation devices that may be useful according to the disclosure are disclosed in U.S. Pat. Nos. 4,922,901, 4,947,874, and 4,947,874, all to Brooks et al., all of which are incorporated herein by reference in their entireties.

In various implementations, the power source used to provide power to the various electrical components of the aerosol delivery device may take on various implementations. Preferably, the power source may fit inside of the housing and may be able to deliver sufficient energy to rapidly heat the heating member in the manner described above and power the article through use with multiple aerosol source members. One example of a useful power source is a N50-AAA CADNICA nickel-cadmium cell produced by Sanyo Electric Company, Ltd., of Japan. A plurality of such batteries, providing 1.2-volts each, may be connected in series. In other implementations, different power sources, such as rechargeable lithium-manganese dioxide batteries, may be used. Although any of these power sources or combinations thereof may be used, rechargeable batteries may be preferred because of cost and disposal considerations associated with disposable batteries. In addition, if disposable batteries are used, the device may be openable for replacement of the batteries. In implementations where rechargeable batteries are used, the control segment may further comprise charging contacts (not shown), for interaction with corresponding contacts in a conventional recharging unit (not shown) deriving power from a standard 120-volt AC wall outlet, or other sources such as an automobile electrical system or a separate portable power supply. In some implementations, multiple batteries may be used, which may be connected in series or in parallel.

In further implementations, the power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—i.e., an electric double-layer capacitor (EDLC)—may be used separate from or in combination with a battery. When used alone, the supercapacitor may be recharged before each use of the device. Thus, the present disclosure may also include a charger component that can be attached to the device between uses to replenish the supercapacitor. Thin film batteries may be used in certain implementations of the disclosure.

As noted above, in various implementations, the aerosol delivery device may comprise one or more indicators (not shown). In some implementations, such indicators may be lights (e.g., light emitting diodes) that may provide indication of multiple aspects of use of the device. For example, a series of lights may correspond to the number of puffs for a given cartridge. Specifically, the lights may successively become lit with each puff such that when all lights are lit, the consumer is informed that the aerosol source member is spent. Alternatively, all lights may be lit in response to the aerosol source member being inserted into the housing, and a light may turn off with each puff, such that when all lights are off, the consumer is informed that the aerosol source member is spent. In still other implementations, only a single indicator may be present, and lighting thereof may indicate that current was flowing to the heating member and the device is actively heating. This may ensure that a consumer does not unknowingly leave an article unattended in an actively heating mode. In alternative implementations, one or more of the indicators may be a component of the aerosol source member. Although the indicators are described above in relation to visual indicators in an on/off method, other indices of operation also are encompassed. For example, visual indicators also may include changes in light color or intensity to show progression of the smoking experience. Tactile indicators and audible indicators similarly are encompassed by the disclosure. Moreover, combinations of such indicators also may be used in a single device.

Although a variety of materials for use in the present device, such as heaters, batteries, capacitors, switching components, and the like have been described, the disclosure should not be construed as being limited to only the exemplified implementations. Rather, one of skill in the art should recognize based on the present disclosure similar components in the field that may be interchanged with any specific component of the present disclosure. For example, U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. App. Pub. No. 2009/0320863 by Fernando et al. discloses computer interfacing means for smoking devices to facilitate charging and allow computer control of the device; U.S. Pat. App. Pub. No. 2010/0163063 by Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include 4,735,217 to Gerth et al.; U.S. Pat. No. 5,249,586 to Morgan et al.; U.S. Pat. No. 5,666,977 to Higgins et al.; U.S. Pat. No.

6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. App. Pub. Nos. 2009/0095311, 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon. A variety of the materials disclosed by the foregoing documents may be incorporated into the present devices in various implementations, and all of the foregoing disclosures are incorporated herein by reference in their entireties.

It should be further noted that in various implementations the inhalable substance medium of the aerosol source member may be modified as desired to control various aspects of release, amount, and flavor of the aerosol. For example, the inhalable substance may be evenly dispersed on or within the inhalable substance medium so that each respective segment that is heated will release substantially the same content of the inhalable substance. Alternatively, the inhalable substance may be dispersed in an uneven configuration. For example, in one implementation, a first segment of the inhalable substance medium that contacts the heating member may be supercharged with the inhalable substance. For example, a single segment of the inhalable substance medium corresponding to the size of the area heated by the heating member may comprise about 30% to about 90%, about 35% to about 75%, or about 40% to about 60% of the total amount of the inhalable substance present in the inhalable substance medium. Similarly, a single segment, such as the final segment of the inhalable substance medium heated by the heating member, may include a flavor or other material that is different from the remaining portion of the inhalable substance medium. Such final release of flavor or other material may function as a signal to a consumer that the aerosol source member has been completely used. Thus, it can be seen that segmented heating may provide for controlled dosing of the inhalable substance in each heated segment.

Figure 13:
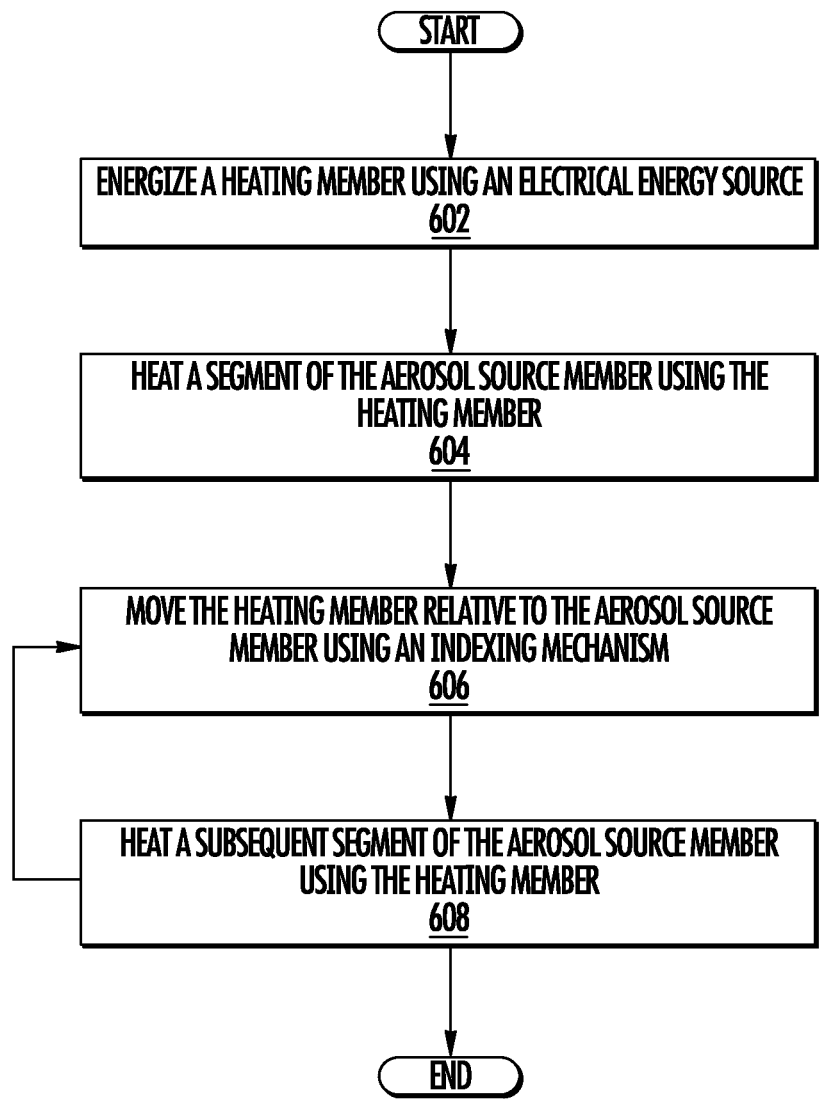
FIG. 13 illustrates various operations in a method of operation of an aerosol delivery device, in accordance with an example implementation of the present disclosure.

The present disclosure also provides a method of operating an aerosol delivery device in various implementations. For example, FIG. 13 illustrates various operations in a method 600 of operating an aerosol delivery device that includes a control body and an aerosol source member. As shown at block 602, the method may include energizing a heating member using an electrical energy source located in a housing of the control body. As shown at block 604, the method may also include heating a segment of the aerosol source member using the heating member. As shown at block 606, the method may further include moving the heating member relative to the aerosol source member by moving the heating member from a first position to a second position using an indexing mechanism. In addition, as shown at block 608, the method may also include heating a subsequent segment of the aerosol source member using the heating member. As further shown in the figure, the process of creating incremental motion between the heating member and the aerosol source member may be continued to heat multiple subsequent segments of the aerosol source member. As noted above, in some implementations the temperature of the heating member may remain at a heating temperature before heating a subsequent segment, while in other implementations, the temperature of heating member may change. For example, the temperature of the heating member may be reduced after heating one segment of the aerosol source member and then it may be heated up to the heating temperature before heating the subsequent segment of the aerosol source member.

As also noted above, in some implementations, heating subsequent segments of the aerosol source member may comprise initially heating an external surface of first and second segments of the aerosol source member. In some implementations, heating the first and second segments of the aerosol source member may comprise initially heating an internal surface of the first and second segments of the aerosol source member. In some implementations, the indexing mechanism may be activated using a sensor configured to detect a draw on the aerosol source member. In some implementations, the indexing mechanism may be activated using a manual actuator. In some implementations, the manual actuator may be configured to move with the heating member, while in other implementations, the manual actuator may comprise a click-return actuator. In addition to any advantages as otherwise described herein, in some implementations, an advantage of the incremental relative motion between a heating member and an aerosol source is that the wiping action between these two components may have the effect of helping to keep the surface of the heating member relatively free from any buildup of condensed materials.

It should be noted that for any of the implementations described or contemplated herein, the electrical heating member may comprise an inductive heating member. In various implementations, the inductive heating member may comprise a resonant transmitter and/or a resonant receiver. In such a manner, operation of the aerosol delivery device may require directing alternating current to the resonant transmitter to produce an oscillating magnetic field in order to induce eddy currents in a resonant receiver that is disposed proximate an inhalable substance medium of an aerosol source member. This alternating current causes the resonant receiver to generate heat and thereby creates an aerosol from the inhalable substance medium.

Accordingly, in some implementations the control component of the control body may include an inverter or an inverter circuit configured to transform direct current provided by the power source to alternating current that is provided to the resonant transmitter. As such, in some implementations a resonant transmitter (such as, for example, a coil member disposed proximate an aerosol source member) and an aerosol source member may be moved relative to each other in order to sequentially heat one of two or more segments of the aerosol source member by inductive heating. For example, in some implementations a resonant transmitter may be moved relative to a stationary aerosol source member. In other implementations, an aerosol source member may be moved relative to a stationary resonant transmitter. In still other implementations both a resonant transmitter and an aerosol source member may be moved relative to each other.

In other implementations, a resonant receiver (such as, for example, a receiving rod or prong disposed inside of a hollow aerosol source member) and an aerosol source member may be moved relative to each other in order to sequentially heat one of two or more segments of the aerosol source member by inductive heating. For example, in some implementations a resonant receiver may be moved relative to a stationary aerosol source member. In other implementations, an aerosol source member may be moved relative to a stationary resonant receiver. In still other implementations, both a resonant receiver and an aerosol source member may be moved relative to each other.

In other implementations, a shielding member, which may be configured to shield electromagnetic energy and/or allow a discrete area of electromagnetic energy therethrough, may be moved relative to an aerosol source member in order to sequentially heat one of two or more segments of the aerosol source member by inductive heating. For example, in some implementations, a shielding member may be moved relative to a stationary aerosol source member. In other implementations, an aerosol source member may be moved relative to a stationary shielding member. In still other implementations, both a shielding member and an aerosol source member may be moved relative to each other.

Examples various inductive heating methods and configurations are described in U.S. patent application Ser. No. 15/799,365, filed on Oct. 31, 2017, titled Induction Heated Aerosol Delivery Device, which is incorporated by reference herein in its entirety. Further examples of various induction-based control components and associated circuits are described in U.S. patent application Ser. No. 15/352,153, filed on Nov. 15, 2016, titled Induction-Based Aerosol Delivery Device, and U.S. Patent Application Publication No. 2017/0202266 to Sur et al., each of which is incorporated herein by reference in its entirety.

It should also be noted that although the aerosol source member and control body may be provided together as a complete smoking article or pharmaceutical delivery article generally, the components also may be provided separately. For example, the present disclosure also encompasses a disposable unit for use with a reusable smoking article or a reusable pharmaceutical delivery article. In specific implementations, such a disposable unit (which may be an aerosol source member as illustrated in the appended figures) can comprise a substantially tubular shaped body having a heated end configured to engage the reusable smoking article or pharmaceutical delivery article, an opposing mouth end configured to allow passage of an inhalable substance to a consumer, and a wall with an outer surface and an inner surface that defines an interior space. Various implementations of an aerosol source member (or cartridge) are described in U.S. Pat. No. 9,078,473 to Worm et al., which is incorporated herein by reference.

In addition to the disposable unit, the present disclosure may further be characterized as providing a separate control body for use in a reusable smoking article or a reusable pharmaceutical delivery article. In specific implementations, the control body may generally be a housing having a receiving end (which may include a receiving chamber with an open end) for receiving a heated end of a separately provided aerosol source member. The control body may further include an electrical energy source that provides power to an electrical heating member, which may be a component of the control body or may be included in aerosol source member to be used with the control unit. In various implementations, the control body may also include further components, including an electrical power source (such as a battery), components for actuating current flow into the heating member, and components for regulating such current flow to maintain a desired temperature for a desired time and/or to cycle current flow or stop current flow when a desired temperature has been reached or the heating member has been heating for a desired length of time. In some implementations, the control unit further may comprise one or more pushbuttons associated with one or both of the components for actuating current flow into the heating member, and the components for regulating such current flow. The control body may also include one or more indicators, such as lights indicating the heater is heating and/or indicating the number of puffs remaining for an aerosol source member that is used with the control body.

Although the various figures described herein illustrate the control body and aerosol source member in a working relationship, it is understood that the control body and the aerosol source member may exist as individual devices. Accordingly, any discussion otherwise provided herein in relation to the components in combination also should be understood as applying to the control body and the aerosol source member as individual and separate components.

In another aspect, the present disclosure may be directed to kits that provide a variety of components as described herein. For example, a kit may comprise a control body with one or more aerosol source members. A kit may further comprise a control body with one or more charging components. A kit may further comprise a control body with one or more batteries. A kit may further comprise a control body with one or more aerosol source members and one or more charging components and/or one or more batteries. In further implementations, a kit may comprise a plurality of aerosol source members. A kit may further comprise a plurality of aerosol source members and one or more batteries and/or one or more charging components. In the above implementations, the aerosol source members or the control bodies may be provided with a heating member inclusive thereto. The inventive kits may further include a case (or other packaging, carrying, or storage component) that accommodates one or more of the further kit components. The case could be a reusable hard or soft container. Further, the case could be simply a box or other packaging structure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device, comprising:
a control body having a housing;
an electrical energy source located within the housing;
a heating member operatively connected to the electrical energy source;
an aerosol source member that includes an inhalable substance medium; and
an indexing mechanism coupled to the heating member,
wherein the indexing mechanism is configured to move the heating member relative to the aerosol source member so as to sequentially heat at least one of two or more segments of the aerosol source member, and wherein the indexing mechanism comprises a motor, a lead screw, and a carrier to which the heating member is affixed.

2. The aerosol delivery device of claim 1, wherein the heating member is located proximate an external surface of the aerosol source member.

3. The aerosol delivery device of claim 1, wherein the heating member is located proximate an internal surface of the aerosol source member.

4. The aerosol delivery device of claim 1, wherein the indexing mechanism is activated by a sensor configured to detect a draw on the aerosol source member.

5. The aerosol delivery device of claim 1, wherein the indexing mechanism is activated by a manual button.

6. The aerosol delivery device of claim 1, wherein the aerosol source member is removably engaged with the control body and replaceable.

7. The aerosol delivery device of claim 1, wherein the inhalable substance medium of the aerosol source member comprises a solid or semi-solid inhalable substance medium.

8. The aerosol delivery device of claim 7, wherein the inhalable substance medium comprises an extruded substrate.

9. A control body for use with an aerosol source member that includes an inhalable substance medium, the control body comprising:
   a housing;
   an electrical energy source located within the housing;
   a heating member operatively connected to the electrical energy source; and
   an indexing mechanism coupled to the heating member,
   wherein the indexing mechanism is configured to move the heating member relative to the aerosol source member so as to sequentially heat at least one of two or more segments of the aerosol source member, and wherein the indexing mechanism comprises a motor, a lead screw, and a carrier to which the heating member is affixed.

10. The control body of claim 9, wherein the indexing mechanism is activated by a sensor configured to detect a draw on the aerosol source member.

11. The control body of claim 9, wherein the indexing mechanism is activated by a manual actuator.

12. A method of operating an aerosol delivery device that includes a control body and an aerosol source member, said method comprising:
   energizing a heating member using an electrical energy source located in a housing of the control body;
   heating a first segment of the aerosol source member using the heating member;
   moving the heating member relative to the aerosol source member from a first position to a second position using an indexing mechanism; and
   heating a second segment of the aerosol source member using the heating member,
   wherein the indexing mechanism comprises a motor, a lead screw, and a carrier to which the heating member is affixed.

13. The method of claim 12, wherein heating the first and second segments of the aerosol source member comprises initially heating an external surface of the first and second segments of the aerosol source member.

14. The method of claim 12, wherein heating the first and second segments of the aerosol source member comprises initially heating an internal surface of the first and second segments of the aerosol source member.

15. The method of claim 12, further comprising activating the indexing mechanism using a sensor configured to detect a draw on the aerosol source member.

16. The method of claim 12, further comprising activating the indexing mechanism using a manual actuator.

* * * * *